United States Patent
Wu et al.

(10) Patent No.: US 9,181,244 B1
(45) Date of Patent: Nov. 10, 2015

(54) SUBSTITUTED PYRIDO[2,3-C]PYRIDAZIN-4(1H)-ONES AS TUMOR NECROSIS FACTOR ALPHA AND PHOSPHODIESTERASE 4 INHIBITORS

(71) Applicant: Xuanzhu Pharma Co., Ltd., Shandong (CN)

(72) Inventors: Frank Wu, Shandong (CN); Liang Sun, Shandong (CN)

(73) Assignee: XUANZHU PHARMA CO., LTD., Shandong (CN)

( * ) Notice: Subject to any disclaimer, the term of this patent is extended or adjusted under 35 U.S.C. 154(b) by 0 days.

(21) Appl. No.: 14/338,830

(22) Filed: Jul. 23, 2014

(51) Int. Cl.
*A61K 31/5025* (2006.01)
*C07D 237/26* (2006.01)
*C07D 471/04* (2006.01)

(52) U.S. Cl.
CPC .................................. *C07D 471/04* (2013.01)

(58) Field of Classification Search
CPC .......................... A61K 31/5025; C07D 237/26
USPC .......................... 514/248; 544/236; 546/268.1
See application file for complete search history.

(56) References Cited

FOREIGN PATENT DOCUMENTS

CN          103214478 A       7/2013

OTHER PUBLICATIONS

Vippagunta, et al. Advanced Drug Delivery Reviews, 48, 2001, 18.*
Jordan, V. C. Nature Reviews: Drug Discovery, 2, 2003, 205.*
Hackam, et al. JAMA, 296(14), 2006, 1731-1732.*

English language abstracted for CN103214478 extracted from espacenet.com on Jul. 5, 2014, 1 page, and machine assisted translation extracted from google.com/patents on Jul. 5, 2014, 16 pages.

* cited by examiner

*Primary Examiner* — Douglas M Willis
(74) *Attorney, Agent, or Firm* — Howard & Howard Attorneys PLLC

(57) ABSTRACT

The present invention pertains to field of medical technology, specifically relates to a pyridino-oxopyridazine derivative of formula (I), its pharmaceutically acceptable salts, its stereoisomers or its solvates, wherein $R^1$, $R^2$, $R^3$, $R^4$, $R^5$, $R^6$, $R^7$, $R^8$, $R^9$, $R^{7'}$, $R^{8'}$, $R^{9'}$, L and ring A are defined as the description; the present invention further relates to methods for preparing the compounds, a pharmaceutical composition comprising the compound, and use of the compound and the pharmaceutical composition in manufacture of a medicament for treatment and/or prophylaxis of an inflammatory disease, symptom and condition characterized in undesired inflammatory immunoreaction or associated with undesired inflammatory immunoreaction, as well as all diseases induced by oversecretion of TNF-α and PDE-4 or associated with oversecretion of TNF-α and PDE-4.

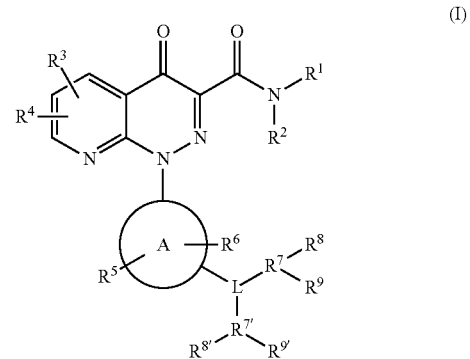

15 Claims, No Drawings

SUBSTITUTED PYRIDO[2,3-C]PYRIDAZIN-4(1H)-ONES AS TUMOR NECROSIS FACTOR ALPHA AND PHOSPHODIESTERASE 4 INHIBITORS

TECHNICAL FIELD

The present invention relates to field of medical technology, specifically relates to a pyridino-oxopyridazine derivative, its pharmaceutically acceptable salts, its stereoisomers or its solvates, their preparation methods, a pharmaceutical composition comprising the compound, and use of the compound and the pharmaceutical composition in manufacture of a medicament for treatment and/or prophylaxis of an inflammatory disease, symptom and condition characterized in undesired inflammatory immunoreaction or associated with undesired inflammatory immunoreaction, as well as all diseases induced by oversecretion of TNF-α and PDE-4 or associated with oversecretion of TNF-α and PDE-4.

BACKGROUND ART

Hormones are a kind of compounds influencing cell activity in different manners. In many cases, hormones act as messengers to trigger specific cellular reactions and activities. However, many effects induced by hormones are not caused by specific effects of hormones. On the contrary, a hormone firstly combines with a receptor, thereby triggering release of a second compound, and the second compound further influences cellular activity. In this case, the hormone is called as first messenger, and the second compound is called as second messenger. Cyclic adenosine monophosphate (adenosine-3",5'-cyclic monophosphate, cAMP or cyclic AMP) is considered as a second messenger of hormones such as adrenaline, glucagon, calcitonin, adrenocorticotrophic hormone, lipotropic hormone, luteinizing hormone, norepinephrine, parathormone, thyroid stimulating hormone and pitressin. Thus, cAMP mediates cellular reaction with hormones, and cAMP also mediates cellular reaction with various neurotransmitter.

Phosphodiesterases (PDEs) have function of hydrolyzing second messengers in cells, degrading cAMP in cells, thereby terminating biochemical action transducted by these second messengers. PDEs family has 11 enzymes, in which PDE4 enzyme is a specific cAMP hydrolase, mainly distributing in airway smooth muscle cells as well as inflammatory cells and immune cells such as lymphocytes, macrophages, neutrophile granulocytes, eosinophilic granulocytes, basophilic granulocytes, mononuclear leucocytes, epithelial cells, regulating cAMP level in these cells.

PDE4 inhibitors can inhibit activities of these immune cells and inflammatory cells, can be used for treatment of diseases caused by inflammations, such as asthma, chronic obstructive pulmonary disease (COPD), rheumatoid arthritis, multiple sclerosis, Alzheimer's disease (AD), Parkinson's disease (PD) and stroke which are central nervous system diseases resulting from neuron injury induced by potential inflammation.

Roflumilast is the first marketed PDE4 inhibitor. Patients with COPD showed a significant decrease in number of neutrophile granulocyte in phlegm after more than 4 weeks of oral administration of Roflumilast, and slight improvement in pulmonary function after more than 6-12 months of oral administration. But it could not significantly alleviate acute exacerbation of symptom or improve life quality, which reason might be the side-effects limited the application dose.

Cilomilast is a PDE4 inhibitor, and is terminated for use at phase III due to adverse reaction of emesis. One concerned problem of using PDE4 inhibitor is side-effects of inducing emesis. Studies have shown that PDE4 has 4 subtypes: PDE4A, 4B, 4C and 4D; wherein PDE4B relates to anti-inflammation, PDE4D also has anti-inflammatory function, but they also relate to central emesis reaction. Some studies have shown that Cilomilast has activity to PDE4D 10 time better than the activity of PDE4B, while Roflumilast has equivalent activity to PDE4B and PDE4D. Therefore, PDE4 inhibitors with equivalent activity to PDE4B and PDE4D would be designed to remarkably reduce side-effect of emesis, increase therapeutic window of drug, and achieve optimal therapeutic effects.

MK-0873 is a drug under study in Merck & Co., and has now entered into clinical phase II. This compound had a module different from Roflumilast and Cilomilast, and data in documents show that it has equivalent activity to various subtypes of PDE4, thereby reducing frequency of adverse effects such as emesis in some extent, increasing therapeutic window and fulfilling better therapeutic effects.

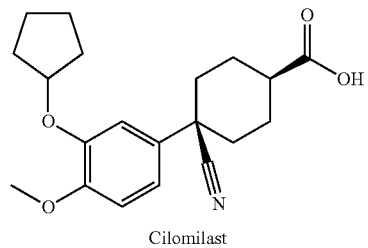 [SMILES: COc1ccc([C@]2(C#N)CC[C@@H](C(=O)O)CC2)cc1OC1CCCC1]

Cilomilast

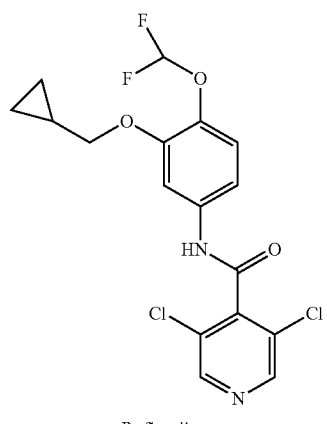

Roflumilast

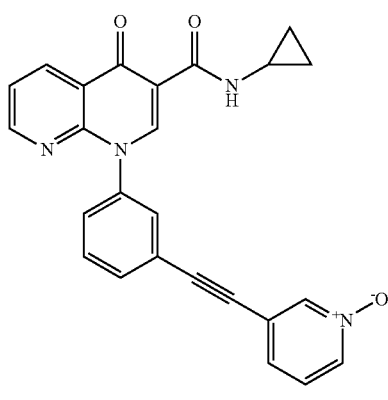

MK-0873

We further optimize the module of MK-0873 compound so as to find desired drug of PDE4 inhibitors to meet clinical requirements.

SUMMARY OF THE INVENTION

The present invention provides a compound of Formula (I) as PDE-4 inhibitor, its pharmaceutically acceptable salts, its stereoisomers or its solvates:

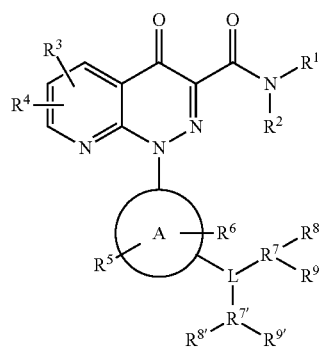

(I)

wherein $R^1$ is hydrogen, $C_{1-8}$ alkyl unsubstituted or substituted with 1-3 substituents, $C_{1-8}$ alkoxy unsubstituted or substituted with 1-3 substituents, $C_{3-8}$ cycloalkyl unsubstituted or substituted with 1-3 substituents, $C_{2-8}$ alkenyl unsubstituted or substituted with 1-3 substituents, $C_{3-8}$ alkynyl unsubstituted or substituted with 1-3 substituents, —C(O)—$R^a$, —S(O)$_q$—$R^a$, $C_{6-14}$ aryl unsubstituted or substituted with 1-3 substituents, 5-15-membered heteroaryl unsubstituted or substituted with 1-3 substituents, or 3- 15-membered heterocycle$C_{1-8}$ alkyl unsubstituted or substituted with 1-3 substituents;

$R^2$ is hydrogen, $C_{1-8}$ alkyl unsubstituted or substituted with 1-3 substituents, or $C_{3-8}$ cycloalkyl unsubstituted or substituted with 1-3 substituents;

each of $R^3$, $R^4$, $R^5$ and $R^6$ independently represents hydrogen, halogen, $C_{1-8}$ alkyl unsubstituted or substituted with 1-3 substituents, $C_{1-8}$ alkoxy unsubstituted or substituted with 1-3 substituents, —C(O)—$R^a$, —S(O)$_q$—$R^a$, nitro, cyano, or —NR$^a$R$^{a\prime}$;

$R^7$ is phenyl, thienyl, pyridonyl, oxazolyl, oxadiazolyl, thiazolyl, or thiadiazolyl, unsubstituted or substituted with 1-3 substituents; unsubstituted or 1-3 substituents-substituted pyridyl, pyrimidyl, indolyl, quinolyl, or imidazolyl and their nitrogen oxides; or hydrogen; $C_{1-8}$ alkyl unsubstituted or substituted with 1-3 substituents; or $C_{3-8}$ cycloalkyl unsubstituted or substituted with 1-3 substituents;

$R^{7\prime}$ is absent, or is phenyl, thienyl, pyridonyl, oxazolyl, oxadiazolyl, thiazolyl, or thiadiazolyl unsubstituted or substituted with 1-3 substituents, unsubstituted or 1-3 substituents-substituted pyridyl, pyrimidyl, indolyl, quinolyl, or imidazolyl and their nitrogen oxides; or hydrogen; $C_{1-8}$ alkyl unsubstituted or substituted with 1-3 substituents; or $C_{3-8}$ cycloalkyl unsubstituted or substituted with 1-3 substituents;

$R^8$ is hydrogen, halogen, nitro, cyano, =N—O—$C_{1-8}$ alkyl, —O—N=$C_{1-8}$ alkyl, —CH(N=NOH)—$C_{1-8}$ alkyl, $C_{1-8}$ alkyl unsubstituted or substituted with 1-3 substituents, $C_{3-8}$ cycloalkyl unsubstituted or substituted with 1-3 substituents, $C_{1-8}$ alkoxy unsubstituted or substituted with 1-3 substituents, $C_{6-14}$ aryl unsubstituted or substituted with 1-3 substituents, 5- 15-membered heteroaryl unsubstituted or substituted with 1-3 substituents, 3- 15-membered heterocycleC$_{1-8}$ alkyl unsubstituted or substituted with 1-3 substituents, —NR$^a$R$^{a\prime}$, —C(O)—$R^a$, —C(O)NR$^a$R$^{a\prime}$, —NR$^a$C(O)R$^{a\prime}$, —S(O)$_q$—$R^a$, —S(O)$_q$—NR$^a$R$^{a\prime}$, —NR$^a$—S(O)$_q$—R$^{a\prime}$, or —C(O)OR$^a$ group;

$R^{8\prime}$ is absent, or is hydrogen, halogen, nitro, cyano, =N—O—$C_{1-8}$ alkyl, —O—N=$C_{1-8}$ alkyl, —CH(N=NOH)—$C_{1-8}$ alkyl, $C_{1-8}$ alkyl unsubstituted or substituted with 1-3 substituents, $C_{3-8}$ cycloalkyl unsubstituted or substituted with 1-3 substituents, $C_{1-8}$ alkoxy unsubstituted or substituted with 1-3 substituents, $C_{6-14}$ aryl unsubstituted or substituted with 1-3 substituents, 5- 15-membered heteroaryl unsubstituted or substituted with 1-3 substituents, 3- 15-membered heterocycle$C_{1-8}$ alkyl unsubstituted or substituted with 1-3 substituents, —NR$^a$R$^{a\prime}$, —C(O)—$R^a$, —C(O)NR$^a$R$^{a\prime}$, —NR$^a$C(O)R$^{a\prime}$, —S(O)$_q$—$R^a$, —S(O)$_q$—NR$^a$R$^{a\prime}$, —NR$^a$—S(O)$_q$—R$^{a\prime}$, or —C(O)OR$^a$ group;

$R^9$ is hydrogen, hydroxy, halogen, $C_{1-8}$ alkyl unsubstituted or substituted with 1-3 substituents, or —NR$^b$R$^{b\prime}$;

$R^{9\prime}$ is absent, or is hydrogen, hydroxy, halogen, $C_{1-8}$ alkyl unsubstituted or substituted with 1-3 substituents, or —NR$^b$R$^{b\prime}$;

ring A is benzene ring, 5- 8-membered mono-heteroaryl containing 1-4 hetero atoms selected from N, S and O, or 8-14-membered diheterocycle ring group containing 1-4 hetero atoms selected from N, S and O;

L is

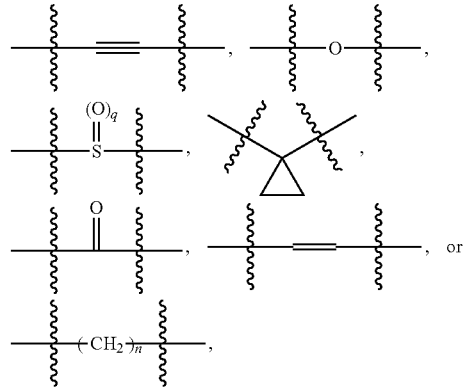

q represents 0, for 2, n represents an integer of 1 to 4;

$R^a$, $R^{a\prime}$ is selected from hydrogen, $C_{1-8}$ alkyl unsubstituted or substituted with 1-3 substituents, $C_{3-8}$ cycloalkyl unsubstituted or substituted with 1-3 substituents, $C_{3-8}$ cycloalkyl$C_{1-8}$ alkyl unsubstituted or substituted with 1-3 substituents, $C_{6-14}$ aryl unsubstituted or substituted with 1-3 substituents, or unsubstituted or 1-3 substituents-substituted 3- 15-membered heterocycle group;

In "substituted $C_{1-8}$ alkyl", "substituted $C_{1-8}$ alkoxy", "substituted $C_{2-8}$ alkenyl", "substituted $C_{3-8}$ alkynyl", "substituted $C_{3-8}$ cycloalkyl", "substituted $C_{3-8}$ cycloalkyl $C_{1-8}$ alkyl", "substituted $C_{6-14}$ aryl", "substituted 5- 15-membered hetero aryl", "substituted 3-15-membered heterocycle group", "substituted 3- 15-membered heterocycle$C_{1-8}$ alkyl", "substituted phenyl, pyridyl, pyrimidyl, indolyl, quinolyl, thienyl, pyridonyl, oxazolyl, oxadiazolyl, thiazolyl, thiadiazolyl, or imidazolyl", substituents refer to one or more groups independently selected from hydroxy, carboxyl, nitro, cyano, halogen, $C_{1-8}$ alkyl, $C_{3-8}$ cycloalkyl, $C_{1-8}$ alkoxy, halogenated $C_{1-8}$ alkyl, halogenated $C_{1-8}$ alkoxy, —NR$^b$R$^{b\prime}$, —C(O)—R$^b$, —C(O)NR$^b$R$^{b\prime}$, —NR$^b$C(O)R$^{b\prime}$, =N—O—$C_{1-8}$ alkyl, —O—N=$C_{1-8}$ alkyl, —S(O)$_q$—R$^b$, —S(O)$_q$—NR$^b$R$^{b\prime}$, —NR$^b$—S(O)$_q$—R$^{b'}$, or —C(O)OR$^b$, wherein each of R$^b$ and R$^{b'}$ independently represents hydrogen, C$_{1-8}$ alkyl, C$_{3-8}$ cycloalkyl or C$_{6-14}$ aryl.

DETAILED DESCRIPTION OF THE DISCLOSURE

The present invention preferably provides a compound of Formula (I), its pharmaceutically acceptable salts, its stereoisomers or its solvates:

wherein R$^1$ is hydrogen, C$_{1-8}$ alkyl unsubstituted or substituted with 1-3 substituents, C$_{1-8}$ alkoxy unsubstituted or substituted with 1-3 substituents, C$_{3-8}$ cycloalkyl unsubstituted or substituted with 1-3 substituents, —C(O)—R$^a$, —S(O)$_q$—R$^a$, C$_{6-14}$ aryl unsubstituted or substituted with 1-3 substituents, or 5- 15-membered hetero aryl unsubstituted or substituted with 1-3 substituents;

R$^2$ is hydrogen, or C$_{1-8}$ alkyl unsubstituted or substituted with 1-3 substituents;

each of R$^3$, R$^4$, R$^5$ and R$^6$ independently represents hydrogen, halogen, C$_{1-8}$ alkyl unsubstituted or substituted with 1-3 substituents, C$_{1-8}$ alkoxy unsubstituted or substituted with 1-3 substituents, —C(O)—R$^a$, —S(O)$_q$—R$^a$, nitro, cyano, or —NR$^a$R$^{a'}$;

R$^7$ is phenyl, thienyl, pyridonyl, oxazolyl, oxadiazolyl, thiazolyl, or thiadiazolyl, unsubstituted or substituted with 1-3 substituents; unsubstituted or 1-3 substituents-substituted pyridyl, pyrimidyl, indolyl, quinolyl, or imidazolyl and their nitrogen oxides;

R$^{7'}$ is absent, or is phenyl, thienyl, pyridonyl, oxazolyl, oxadiazolyl, thiazolyl, or thiadiazolyl, unsubstituted or substituted with 1-3 substituents; unsubstituted or 1-3 substituents-substituted pyridyl, pyrimidyl, indolyl, quinolyl, or imidazolyl and their nitrogen oxides;

R$^8$ is hydrogen, halogen, C$_{1-8}$ alkyl unsubstituted or substituted with 1-3 substituents, —NR$^a$R$^{a'}$, —C(O)—R$^a$, —C(O)NR$^a$R$^{a'}$, —NR$^a$C(O)R$^{a'}$, —S(O)$_q$—R$^a$, —S(O)$_q$—NR$^a$R$^{a'}$, —NR$^a$—S(O)$_q$—R$^{a'}$, or —C(O)OR$^a$ group;

R$^{8'}$ is absent, or is hydrogen, halogen, C$_{1-8}$ alkyl unsubstituted or substituted with 1-3 substituents, —NR$^a$R$^{a'}$, —C(O)—R$^a$, —C(O)NR$^a$R$^{a'}$, —NR$^a$C(O)R$^{a'}$, —S(O)$_q$—R$^a$, —S(O)$_q$—NR$^a$R$^{a'}$, —NR$^a$—S(O)$_q$—R$^{a'}$, or —C(O)OR$^a$ group;

R$^9$ is hydrogen, hydroxy, halogen, C$_{1-8}$ alkyl unsubstituted or substituted with 1-3 substituents;

R$^{9'}$ is absent, or is hydrogen, hydroxy, halogen, C$_{1-8}$ alkyl unsubstituted or substituted with 1-3 substituents;

ring A is benzene ring, 5- 8-membered mono-heteroaryl containing 1-4 hetero atoms selected from N, S and O, or 8- 14-membered diheterocycle group containing 1-4 hetero atoms selected from N, S and O;

L is

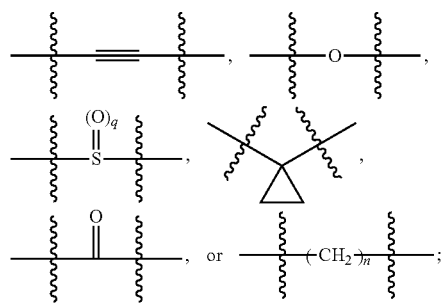

q represents 0, 1 or 2, n represents 1 or 2;

R$^a$ and R$^{a'}$ are selected from hydrogen, C$_{1-8}$ alkyl unsubstituted or substituted with 1-3 substituents;

In "substituted C$_{1-8}$ alkyl", "substituted C$_{1-8}$ alkoxy", "substituted C$_{3-8}$ cycloalkyl", "substituted C$_{6-14}$ aryl", "substituted 5- 15-membered heteroaryl", "substituted 3-15-membered heterocycleC$_{3-8}$ alkyl", "substituted phenyl, pyridyl, pyrimidyl, indolyl, quinolyl, thienyl, pyridonyl, oxazolyl, oxadiazolyl, thiazolyl, thiadiazolyl, or imidazolyl", substituents refer to one or more groups independently selected from hydroxy, carboxyl, cyano, halogen, C$_{1-8}$ alkyl, C$_{3-8}$ cycloalkyl, alkoxy, halogenated C$_{1-8}$ alkoxy, —NR$^b$R$^{b'}$, —C(O)—R$^b$, —C(O)NR$^b$R$^{b'}$, —NR$^b$C(O)R$^{b'}$, —S(O)$_q$—R$^b$, —S(O)$_q$—NR$^b$R$^{b'}$, —NR$^b$—S(O)$_q$—R$^{b'}$, or —C(O)OR$^b$, wherein each of R$^b$ and R$^{b'}$ independently represents hydrogen or C$_{1-8}$ alkyl In another aspect, the present invention relates to a compound of Formula (I), its pharmaceutically acceptable salts, its stereoisomers or its solvates, wherein R$^1$ is hydrogen, methyl, ethyl, propyl, isopropyl, cyclopropyl, cyclobutyl, or cyclopentyl;

R$^2$ is hydrogen, or methyl;

each of R$^3$, R$^4$, R$^5$ and R$^6$ independently represents hydrogen, methyl, fluorine atom, chlorine atom, or bromine atom;

each of R$^8$ and R$^9$ independently represents hydrogen, methyl, fluorine atom, chlorine atom, methylsulfonyl, or 2-hydroxyisopropyl;

R$^{7'}$ is absent;

R$^{8'}$, R$^{9'}$ is absent.

In another aspect, the present invention relates to a compound of Formula (I), its pharmaceutically acceptable salts, its stereoisomers or its solvates, wherein ring A is benzene ring, or 5- 6-membered mono-heteroaryl containing 1-3 hetero atoms selected from N, S and O.

In another aspect, the present invention relates to a compound of Formula (I), its pharmaceutically acceptable salts, its stereoisomers or its solvates, wherein ring A is benzene ring, or 5- 6-membered mono-heteroaryl containing 1-3 N hetero atoms.

In another aspect, the present invention relates to a compound of Formula (I), its pharmaceutically acceptable salts, its stereoisomers or its solvates, wherein ring A is benzene ring, pyrrolyl, imidazolyl, pyrazolyl, triazolyl, pyridyl, pyrimidyl or pyrazinyl.

In another aspect, the present invention relates to a compound of Formula (I), its pharmaceutically acceptable salts, its stereoisomers or its solvates, wherein L is

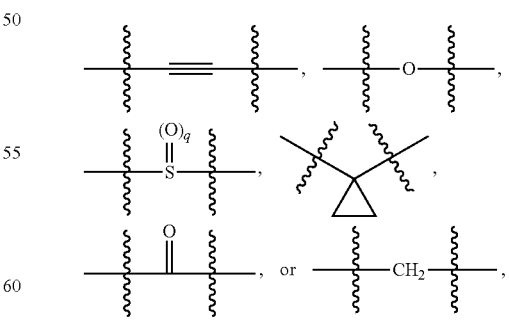

q represents 0, 1 or 2.

In another aspect, the present invention relates to a compound of Formula (I), its pharmaceutically acceptable salts, its stereoisomers or its solvates, wherein L is

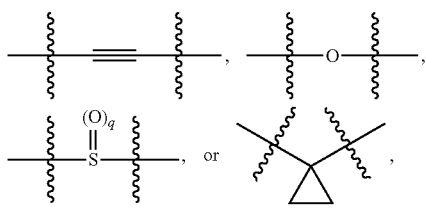

q represents 0, 1 or 2.

In another aspect, the present invention relates to a compound of Formula (I), its pharmaceutically acceptable salts, its stereoisomers or its solvates, wherein $R^7$ is pyridyl or nitrogen oxides thereof.

In another aspect, the present invention relates to a compound of Formula (I), its pharmaceutically acceptable salts, its stereoisomers or its solvates, wherein $R^7$ is pyridyl or nitrogen oxides thereof;
ring A is benzene ring, pyridyl, pyrimidyl or pyrazinyl;
L is

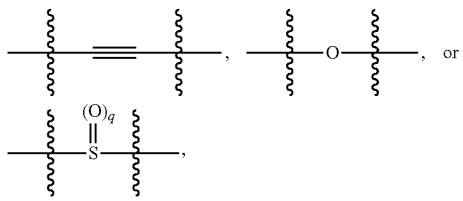

q represents 0, 1 or 2.

In the present invention, the examples of "halogen" include fluorine atom, chlorine atom, bromine atom, iodine atom.

In the present invention, the "$C_{1-8}$ alkyl" refers to a straight or branched alkyl which is derived from a hydrocarbon containing 1-8 carbon atoms by removing one hydrogen atom, examples thereof include but are not limited to methyl, ethyl, n-propyl, isopropyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, n-octyl, 2-methylheptyl, 3-methylheptyl, 4-methylheptyl, 2,2-dimethylhexyl, 3,3-dimethylhexyl, 2,3-dimethylhexyl, 2,4-dimethylhexyl, 2,5-dimethylhexyl, 3,4-dimethylhexyl, 3-ethylhexyl, 2,2,3-trimethylpentyl, 2,2,4-trimethylpentyl, 2,3,3-trimethylpentyl, 2,3,4-trimethylpentyl, 2-methyl-3-ethylpentyl, 3-methyl-3-ethylpentyl, 2,2,3,3-tetramethylbutyl.

In the present invention, the "$C_{1-8}$ alkoxy" refers to a group in which "$C_{1-8}$ alkyl" links to its main structure via oxygen atom, examples thereof include but are not limited to methoxy, ethoxy, propoxy, isopropoxy, butoxy, isobutoxy, tert-butoxy, sec-butoxy, pentoxy, neo-pentoxy, hexoxy, heptoxy, octoxy.

In the present invention, the "$C_{3-8}$ cycloalkyl" refers to a cyclic alkyl containing 3-8 carbon atoms, specific examples thereof include but are not limited to cyclopropyl, cyclobutyl, cyclopentyl, cyclohexyl, cycloheptyl, cyclooctyl.

In the present invention, the "$C_{2-8}$ alkenyl" refers to a straight or branched aliphatic hydrocarbonyl containing C=C double bond and having carbon atom number of 2-8, examples thereof include but are not limited to ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 1,4-hexadienyl, 1-heptenyl, 2-heptenyl, 3-heptenyl, 4-heptenyl, 5-heptenyl, 6-heptenyl, 1-methyl-1-hexenyl, 2-methyl-1-hexenyl, 3-methyl-1-hexenyl, 4-methyl-1-hexenyl, 5-methyl-1-hexenyl, 1-methyl-2-hexenyl, 2-methyl-2-hexenyl, 3-methyl-2-hexenyl, 4-methyl-2-hexenyl, 5-methyl-2-hexenyl, 1-methyl-3-hexenyl, 2-methyl-3-hexenyl, 3-methyl-3-hexenyl, 4-methyl-3-hexenyl, 5-methyl-3-hexenyl, 1-methyl-4-hexenyl, 2-methyl-4-hexenyl, 3-methyl-4-hexenyl, 4-methyl-4-hexenyl, 5-methyl-4-hexenyl, 1-methyl-5-hexenyl, 2-methyl-5-hexenyl, 3-methyl-5-hexenyl, 4-methyl-5-hexenyl, 5-methyl-5-hexenyl, 1,1-dimethyl-2-pentenyl, 1,1-dimethyl-3-pentenyl, 1,1-dimethyl-4-pentenyl, 1,2-dimethyl-1-pentenyl, 2,2-dimethyl-3-pentenyl, 2,2-dimethyl-4-pentenyl, 3,3-dimethyl-1-pentenyl, 3,3-dimethyl-4-pentenyl, 4,4-dimethyl-1-pentenyl, 4,4-dimethyl-2-pentenyl, 1-octenyl, 2-octenyl, 3-octenyl, 4-octenyl, 5-octenyl, 6-octenyl, 7-octenyl.

In the present invention, the "$C_{3-8}$ alkynyl" refers to a straight or branched alkynyl containing C≡C triple bond and 3-8 carbon atoms, examples thereof include but are not limited to 1-propynyl, 2-propynyl, 1-butynyl, 2-butynyl, 3-butynyl, 3-methyl-1-butynyl, 1-pentynyl, 2-pentynyl, 3-pentynyl, 3-methyl-1-pentynyl, 4-methyl-1-pentynyl, 4-methyl-2-pentynyl, 1-hexynyl, 2-hexynyl, 3-hexynyl, 3-methyl-1-hexynyl, 3,4-dimethyl-1-hexynyl, 1-heptynyl, 2-heptynyl, 3-heptynyl, 4-heptynyl, 5-heptynyl, 4-methyl-1-heptynyl, 1-octynyl, 2-octynyl, 3-octynyl, 4-octynyl, 4-ethyl-1-hexynyl.

In the present invention, the "$C_{6-14}$ aryl" refers to an aromatic group containing 6-14 carbon atoms, includes 6-8-membered mono-cyclic aryl and 8-14-membered fused ring aryl. The 6-8-membered mono-cyclic aryl refers to fully unsaturated aryl, such as phenyl, cyclooctatetraenyl. The 8-14-membered fused ring aryl refers to a fused ring group that has at least one ring as unsaturated aromatic ring and is formed by sharing two adjacent carbon atoms of two or more ring structures, including 8-14-membered unsaturated fused ring aryl, such as naphthalenyl, phenanthrenyl, as well as 8-14-membered partially saturated fused ring aryl, such as benzo $C_{3-8}$ cycloalkyl, benzo $C_{4-8}$ cycloalkenyl, specific examples include 2,3-dihydro-1H-indenyl, 1H-indenyl, 1,2,3,4-tetrahydronaphthalenyl, 1,4-dihydronaphthalenyl.

In the present invention, the "5- 15-membered heteroaryl" refers to an unsaturated aromatic ring group containing 5-15 ring atoms (in which at least one is hetero atom), includes 5-8-membered mono-heteroaryl, 6- 15-membered fused heteroaryl, wherein the hetero atom comprises nitrogen, oxygen and sulfur, it also contains carbon atoms, and nitrogen atom and sulfur atom can be replaced with oxygen.

The "5- 8-membered mono-heteroaryl" refers to an aromatic ring group containing 5-8 ring atoms (in which at least one is hetero atom), specific examples include but are not limited to furyl, thienyl, pyrrolyl, thiazolyl, iso-thiazolyl, thiadiazolyl, oxazolyl, iso-oxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,3,4-triazinyl, 1,2,4,5-tetrazinyl, oxacycloheptatrienyl, thiocycloheptatrienyl, azacycloheptatrienyl, 1,3-diazacycloheptatrienyl, azacyclooctatetraenyl, 1,4-dihydro-1,4-diazacyclooctatrienyl, 1,4-dioxacyclooctatrienyl. The "5- 6-member mono-heteroaryl" refers to an aromatic ring group containing 5-6 ring atoms (in which at least one is hetro atom), and specific examples thereof can be seen in specific examples of "5- 8-membered mono-heteroaryl" that contains 5-6 ring atoms.

The "6- 15 fused heteroaryl" refers to an unsaturated aromatic fused ring structure that contains 6-15 ring atoms (in which at least one is hetero atom) and is formed by linking two or more ring structures by sharing two adjacent atoms, the specific examples thereof include but are not limited to benzofuryl, benzoisofuryl, benzothienyl, indolyl, isoindolyl, benzooxazolyl, benzoimidazolyl, indazolyl, benzotriazolyl, quinolyl, 2-quinolinonyl, 4-quinolinonyl, 1-isoquinolinonyl, isoquinolyl, acridinyl, phenanthridinyl, benzopyridazinyl, phthalazinyl, quinazolinyl, quinoxalinyl, phenazinyl, pteridinyl, purinyl, naphthyridinyl, phenazinyl, phenothiazinyl, benzotrifuryl.

In the present invention, the "3- 15-membered heterocycle group" refers to a stable 3-15-membered ring consisting of carbon atoms and 1-5 hetero atoms selected from nitrogen, oxygen, sulfur and phosphorus, can be a monocyclic, dicyclic or tricyclic system, can comprise fused ring, bridged ring or spiral ring system, and hetero atoms in the hetero ring group can be optionally oxidized to form various oxidation states, nitrogen atom can be optionally quaternized, and the hetero ring group can be unsaturated, partially saturated, or fully saturated. The examples of this hetero ring group include but are not limited to the following groups:

The examples of "saturated monocyclic group" include but are not limited to oxacyclopropyl, thiocyclopropyl, azacyclopropyl, oxacyclobutyl, thiocyclobutyl, azacyclobutyl, tetrahydrofuryl, tetrahydrothienyl, pyrrolidinyl, oxazolidinyl, iso-oxazolidinyl, thiazolidinyl, iso-thiazolidinyl, dioxacyclopentyl, dithiocyclopentyl, imidazolidinyl, pyrazolidinyl, dioxaphospholanyl, tetrahydropyranyl, piperidyl, piperazinyl, morpholinyl, thiomorpholinyl, perhydrogenated azepinyl, thiomorpholinylsulfinyl, thiomorpholinylsulfonyl, 2-oxopiperazinyl, 2-oxopiperidyl, 2-oxopyrrolidinyl, 2-oxoazatropylidenyl, 4-piperidonyl; The examples of "partially saturated monocyclic group" include but are not limited to dihydrothienyl, dihydrooxazolyl, dihydroiso-oxazolyl, dihydrothiazolyl, dihydroimidazolyl, dihydropyrazolyl;

The examples of "unsaturated monocyclic group" include but are not limited to furyl, thienyl, pyrrolyl, imidazolyl, pyrazolyl, oxazolyl, iso-oxazolyl, oxadiazolyl, thiazolyl, isothiazolyl, thiadiazolyl, triazolyl, tetrazolyl, pyridyl, pyrazinyl, pyrimidyl, pyridazinyl, azepinyl;

The "saturated bicyclic group" includes saturated fused ring group, saturated bridged ring group and saturated spiral ring group, the examples thereof include but are not limited to "saturated fused ring group" such as decahydroisoquinolyl, octahydroindolyl, octahydroisoindolyl, "saturated bridged ring group" such as

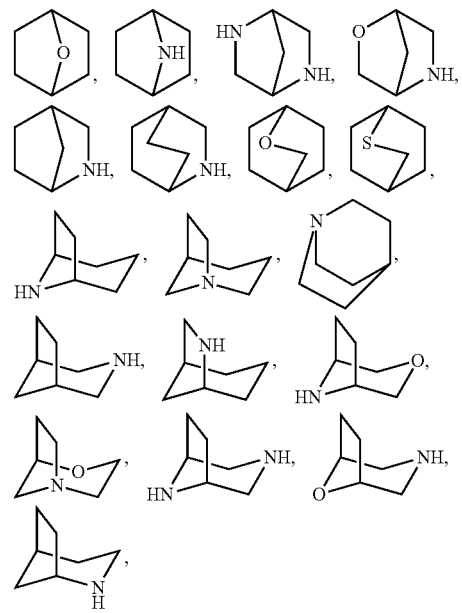

"saturated spiral ring group" such as

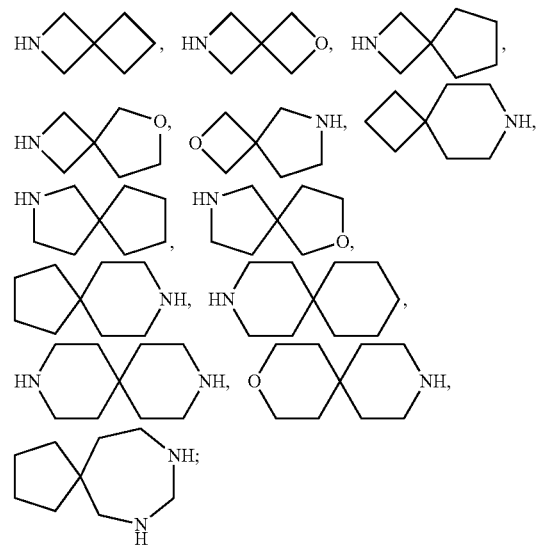

The "partially saturated bicyclic group" includes partially saturated fused ring groups, partially saturated bridged ring groups and partially saturated spiral ring groups, the examples thereof include but are not limited to, "partially saturated fused ring group" such as benzodioxolyl, benzodioxanyl, chromanyl, tetrahydroisoquinolyl, 2,3-dihydroindenyl, dihydroindolyl, dihydroisoindolyl, "partially saturated bridged ring groups" such as

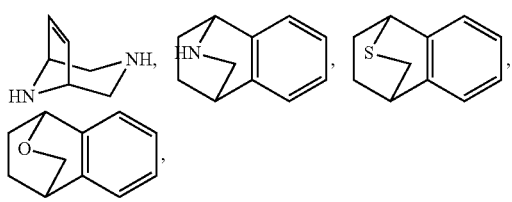

"partially saturated spiral ring group" such as

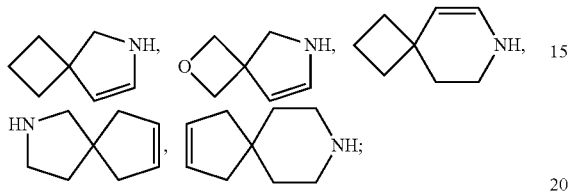

The examples of "unsaturated bicyclic group" include but are not limited to benzofuryl, isobenzofuryl, benzopyranyl, benzothiazolyl, benzooxazolyl, benzoimidazolyl, benzothienyl, isobenzothienyl, indazolyl, benzotriazolyl, cinnolinyl, indolizinyl, naphthyridinyl, pteridinyl, purinyl, quinazolinyl, quinoxalinyl, quinolyl, isoquinolyl, indolyl, isoindolyl, phthalazinyl, quinolinonyl;

The examples of "tricyclic group" include but are not limited to acridinyl, phenanthridinyl, carbazolyl, phenazinyl phenothiazinyl, phenoxazinyl, dibenzofuryl.

In the present invention, the "8- 14-membered dihetero ring group" refers to the above "3-15-membered hetero ring groups" specific examples of "saturated dicyclic", "partially saturated dicyclic" and "unsaturated dicyclic" having 8-14 ring atoms.

In the present invention, the "3- 15-membered heterocycle $C_{1-8}$ alkyl" refers to a group in which "3- 15-membered heterocycle group" links to main structure via a carbon atom of $C_{1-8}$ alkyl, includes but is not limited to pyridin-4-ylmethyl, indol-5-ylethyl.

In the present invention, the "halogenated" in "halogenated $C_{1-8}$ alkyl, halogenated $C_{1-8}$ alkoxy" refers to one or more hydrogen atoms on carbon atoms of $C_{1-8}$ alkyl, $C_{1-8}$ alkoxy are replaced with halogen atoms, and the term "halogen atoms" has the above meanings.

More specifically, the present invention relates to a group of compounds selected from the follows:

| Compound | Structural Formula |
|---|---|
| 1 | 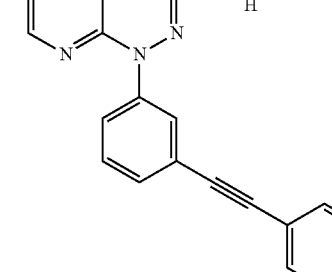 |
| Nitrogen oxide of 1 | 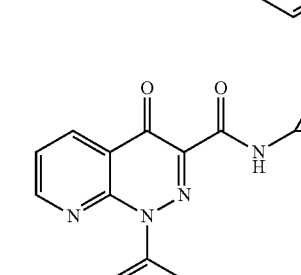 |
| 2 | 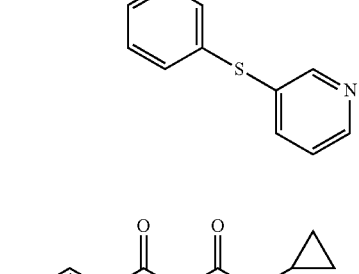 |
| Nitrogen oxide of 2 | 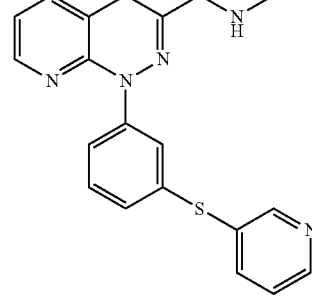 |
| 3 |  |

-continued

| Compound | Structural Formula |
|---|---|
| Nitrogen oxide of 3 | (structure) |
| 4 | (structure) |
| Nitrogen oxide of 4 | (structure) |

The present invention further relates to a method for preparing a compound of Formula (I) as defined above, in which the reaction scheme is as follows, but is not limited to the following method:

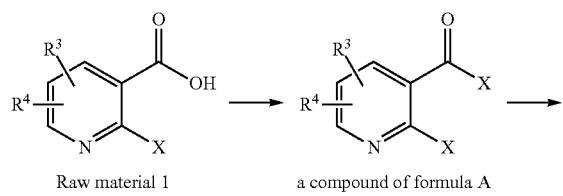

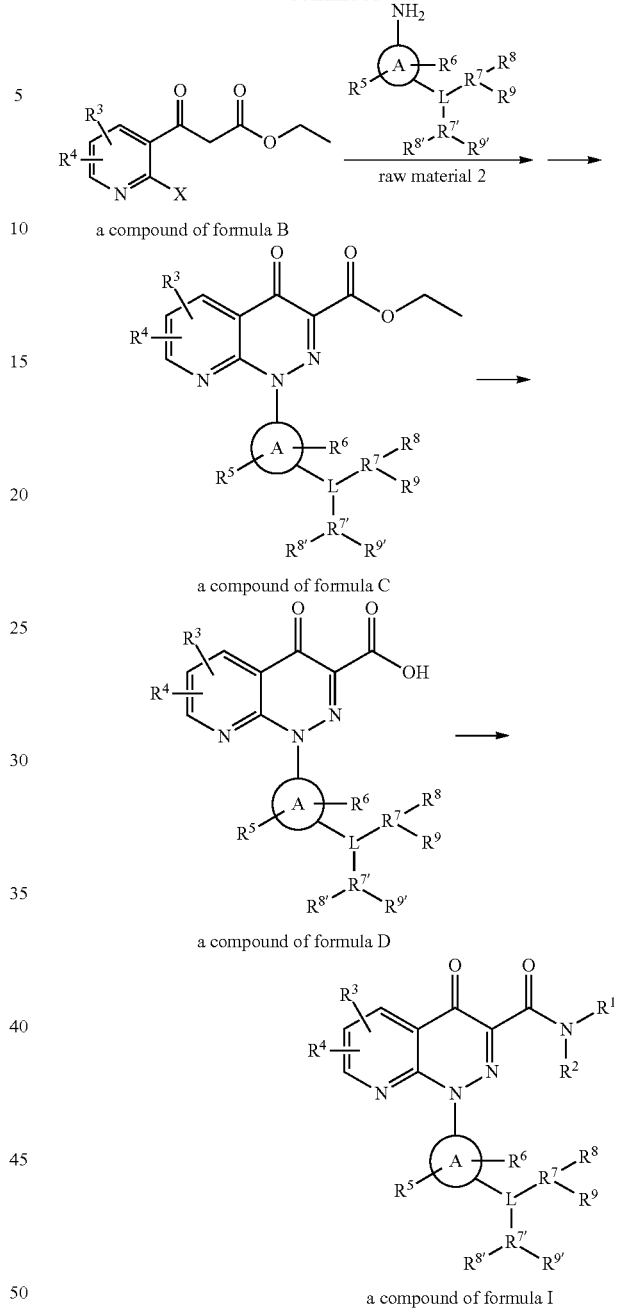

Step 1: Preparation of a Compound of Formula A

Raw material 1 was dissolved in thionyl chloride, reacted at 60-80° C. for 1-5 h, concentrated to obtain the compound of formula A.

Step 2: Preparation of a Compound of Formula B

3-Ethoxy-3-carbonylpropionic acid was dissolved in tetrahydrofuran, n-butyl lithium was dropwise added at 65-85° C., subjected to react at a low temperature for 0.5-2 h, a solution of the compound of formula A in tetrahydrofuran was added, low temperature was kept to perform reaction for 2-4 h, after reaction was complete, extraction was performed with water/dichloromethane, organic phase was rotated for dryness, and separated by column chromatography to obtain the compound of formula B.

Step 3: Preparation of a Compound of Formula C

Under ice-bath, aqueous solution of $NaNO_2$ was added to hydrochloric acid solution of amine, stirred for about 30 min, added to the compound of formula B and sodium acetate in a mixture solvents of ethanol/water/chloroform, reacted under ice-bath for 10-20 min, heated to reach room temperature and reacted for 20-40 min, after reaction was complete, water was added, separated, organic phase was retained and rotated for dryness, to which acetonitrile was added, $K_2CO_3$ was added. The reaction system was heated until refluxing, reacted for 2.5-3.5 h. After reaction was complete, solvent was removed by distillation. Crystallization was performed with ethyl ether to obtain the compound of formula C.

Step 4: Preparation of a Compound of Formula D

The compound of formula C was dissolved in tetrahydrofuran and methanol, a solution of KOH in methanol was added, reacted at 60-80° C. for 3-5 h, adjusted with hydrochloric acid to reach a pH of about 5. Filtration by suction was performed to obtain solid and filter cake was dried to obtain the compound of formula D.

Step 5: Preparation of a Compound of Formula I

The compound of Formula D was dissolved in dichloromethane, and triethylamine and isopropyl chloroformate were added at about −15° C., and reaction was performed at low temperature for 3-5 h, substituted amine was added at low temperature, triethylamine was reacted at room temperature under stifling for 10-14 h, washed with water, concentrated to obtain the compound of Formula I.

In the above reaction scheme, groups $R^1$, $R^2$, $R^3$, $R^4$, $R^5$, $R^6$, $R^7$, $R^8$, $R^9$, $R^{7'}$, $R^{8'}$, $R^{9'}$, L, ring A are the same as mentioned above, X is halogen atom.

The pharmaceutically acceptable salts of any one of the above compounds of the present invention refer to salts as prepared with pharmaceutically acceptable nontoxic alkali or acid, including salts of organic acid, salts of inorganic acid, salts of organic alkali, and salts of inorganic alkali. The salts of organic acid include salts of formic acid, acetic acid, benzene sulfonic acid, benzoic acid, p-toluene sulfonic acid, camphor sulfonic acid, citric acid, methane sulfonic acid, ethane sulfonic acid, propane sulfonic acid, fumaric acid, gluconic acid, glutamic acid, hydroxyethylsulfonic acid, lactic acid, maleic acid, malic acid, mandelic acid, galactaric acid, pamoic acid, pantothenic acid, succinic acid, tartaric acid. The salts of inorganic acid include salts of hydrobromic acid, hydrochloric acid, nitric acid, sulfuric acid, phosphoric acid. Salts of organic alkali include salts of primary, secondary, tertiary amines, substituted amines including natural substituted amines, cyclamines and alkaline ion exchange resin, which are selected from betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, meglumine, glucosamine, hydrabamine, isopropylamine, methylglucosamine, morpholine, piperazine, piperidine, procaine, purine, theobromine, triethylamine, trimethylamine, tripropylamine, tromethamine. Salts of natural amino acids such as salts of glycine, alanine, valine, leucine, isoleucine, norleucine, tyrosine, cystine, cysteine, methionine, proline, hydroxyproline, histidine, ornithine, lysine, arginine, serine. Salts of inorganic alkali include salts of ammonium, lithium, sodium, potassium, calcium, magnesium, zinc, barium, aluminum, ferrum, copper, ferrous, manganese, divalent manganese. Salts in solid form can exist in form of solvates, for example, hydrates.

The compounds of the present invention have one or more asymmetry centers, and thus can be racemes and racemic mixtures, single enantiomers, mixtures of diastereoisomers, and single diastereoisomers. The compounds of the present invention have asymmetry centers, and these asymmetry centers each independently generates two optical isomers, and the scope of the present invention covers all possible optical isomers and mixtures of diastereoisomers, and pure or partially pure compounds. The present invention comprises all stereoisomers of these compounds.

When the compounds of the present invention have alkene double bond, the present invention comprises cis-isomer and trans-isomer unless otherwise specified.

The compounds of the present invention can exist in tautomeric form, and have different hydrogen connection points via movement of one or more double bond. For example, ketone and its enol form are ketone-enol tautomers. All tautomers and mixtures thereof are compounds of the present invention.

The compound of Formula (I), its pharmaceutically acceptable salts, its stereoisomers can be in form of solvates. When solvents are hydrates, hydration can be performed during preparation process or performed by gradual hygroscopicity of original anhydrous product.

Another object of the present invention is to provide a method for treating an inflammatory disease, symptom and condition characterized in undesired inflammatory immunoreaction or associated with undesired inflammatory immunoreaction, as well as all diseases induced by oversecretion of TNF-α and PDE-4 or associated with oversecretion of TNF-α and PDE-4 in a subject, and the method comprises administration of a therapeutically effective amount of a compound of Formula (I) to the subject.

Another object of the present invention is to provide a method for treating inflammatory conditions and immune symptoms in a subject, and the method comprises administration of a therapeutically effective amount of a compound of Formula (I) to the subject.

The preferred inflammatory conditions and immune symptoms are selected from asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohn's disease, psoriasis, urticarial, adult vernal conjunctivitis, respiratory distress, rheumatoid arthritis of spine, osteoarthritis, gouty arthritis, uveitis, allergic conjunctivitis, inflammatory bowel diseases, ulcerative colitis, eczema, atopic dermatitis, chronic inflammations. The preferred is allergic inflammatory diseases.

The further preferred diseases are inflammatory diseases or immune symptoms selected from inflammatory diseases or immune symptoms of lung, joints, eyes, intestines, skin and heart.

The further preferred diseases are inflammatory diseases selected from bronchial asthma, nephritis, and allergic rhinitis.

Another object of the present invention is to provide a method for alleviating inflammation of an involved organ or tissue, the method comprises delivery of a therapeutically effect amount of a compound of Formula (I) to the organ or tissue.

Any one of the compounds of the present invention, its pharmaceutically acceptable salts, its stereoisomers, its nitrogen oxides or solvates, can be administered to a patient in need thereof by oral administration or inhalation administration.

When administering to a patient in need of this therapy by oral administration, it can be processed to form conventional solid preparations for oral administration, such as tablets, capsules, pills, granules; or processed to form oral liquid preparations, such as oral solutions, oral suspensions, and syrups. Tablets refer to solid preparation in form of rounded tablets or shaped tablets formed by mixing and pressing drug and suitable excipients, which mainly comprise normal oral tablets, as well as lozenges, sublingual tablets, buccal tablets, chewable tablets, dispersible tablets, soluble tablets, effervescent tablets, sustained release tablets, controlled release tablets and enteric coated tablets. Capsules refer to solid preparation in which drug optionally combined with excipients are filled in empty capsules or sealed in soft capsule materials. Capsules are classified according to dissolution and release properties to hard capsules (commonly called as capsules), soft capsules (gelatin pills), sustained release capsules, controlled release capsules and enteric capsules. Pills refer to spherical or spheroid solid preparations, which are prepared by a suitable method from a uniform mixture of drug and suitable excipients, including drop pills, sugared pills, pellets. Granules refer to dry granular preparation formed with drug and suitable excipients, can be divided into soluble granules (commonly called as granules), suspension granules, effervescence granules, enteric granules, sustained release granules and controlled release granules. Oral solutions refer to clear liquid preparation for oral administration, which are prepared by dissolving drug in suitable solvent. Oral suspensions refer to suspension liquid preparation for oral administration, in which insoluble solid drug is dispersed in liquid carrier, including dry suspensions or concentrated suspensions. Syrups refer to concentrated sucrose aqueous solutions that contain drug.

For preparation of oral preparations, suitable fillers, binding agents, disintegrating agents, lubricants and so on can be added. Commonly used fillers include starches, sugar powders, calcium phosphate, calcium sulfate dehydrate, dextrin, microcrystalline cellulose, lactose, pre-gelatinized starches, mannitol; commonly used binding agents include carboxymethylcellulose sodium, PVP-K30, hydroxypropylcellulose, starch slurry, methylcellulose, ethylcellulose, hydroxypropylmethylcellulose, gelatinized starches. Commonly used disintegrating agents include dry starch, cross-linked polypyrrolidone, cross-linked carboxymethylcellulose sodium, carboxymethylstarch sodium, low-substituted hydroxypropylcellulose. Commonly used lubricants include magnesium stearate, talc powder, sodium dodecylsulfate, Aerosil.

When the compound of Formula (I) is administrated by inhalation to patient in need of this therapy, it is delivered in form of pressed aerosol. After homogenization, the compound of Formula (I) is micronized, for example, in lactose, glucose, higher aliphatic acids, sodium dioctyl succinate sulfonate, or most preferably in carboxymethylcellulose so that most particles have a particle size of 5 μm or less. Regarding inhalation preparation, aerosol can be mixed with a gaseous or liquid propellant for dispersing active substance. Inhalator or atomizer is used.

The beneficial effects of the compounds of the present invention are further illustrated by following in vitro pharmacological experiments, but it should not be understood that the compounds of the present invention have only the following beneficial effects.

Experiment: In Vitro Pharmacological Activity of the Compounds of the Present Invention Test samples: some compounds of the present invention, MK-0873, self-made, their chemical names and structural formulas are shown above.

Experimental Methods: Lance cAMP Assay:

Test samples were precisely weighed, added to and dissolved in DMSO, mixed sufficiently so as to reach 100 μM. The above mother solution was then diluted with DMSO to reach 1 μM, and then diluted 4 times to reach 0.0038 nM.

To 384 well plate were added 2.5 μl of substrate 20 nM cAMP and 50 nl of compound DMSO solution, then added 2.5 μl of PDE enzyme (PDE4B1 0.18 nM, PDE4D3 0.024 nM) buffer solution (1×HBSS, 5 mM Hepes pH 7.4, 3 mM $MgCl_2$, 0.1% BSA). After incubation at room temperature for 90 min, 5 μl of Alexa Fluor® 647-anti cAMP antibody was added and incubated for 30 min, 10 μl of detection reagent was added and incubated for 60 min, then its LANCE signal was detected under 665 nm, inhibition rate was calculated by the following formulation, and $IC_{50}$ values were calculated from inhibition rate using XLfit.

Inhibition rate=[signal value (MAX)−signl value (sample)]×100/[signal value (MAX)−signal value (MIN)]

Notation: MAX: blank control without enzyme; MIN: blank control without compound.

Experimental results and conclusions:

TABLE 1

$IC_{50}$ values of the compounds of the present invention to PDE-4B1, PDE-4D3

| Compound | PDE-4B1 (nM) | PDE-4D3 (nM) |
| --- | --- | --- |
| MK-0873 | 5.59 | 4.58 |
| Compound 1 | 2.68 | 2.19 |
| Nitrogen oxide of Compound 1 | 28.1 | 18.9 |
| Compound 2 | 160.7 | 250.2 |
| Compound 3 | 304.9 | 357.8 |
| Nitrogen oxide of Compound 3 | 526.2 | 643.5 |

Conclusion: As can be seen in Table 1 that the compound of the present invention has good inhibition activity to PDE-4B1, PDE-4D3; good anti-inflammatory activity; and substantively equivalent inhibition activity to PDE-4B1 and PDE-4D3, and the compound of the present invention has less side-effects such as emesis in clinical use.

Experiment 2: Measurement of Inhibition Activity of TNF-α in Whole Blood Test

Experimental Method:

Fresh blood was collected from health human body using heparin sodium tubes. In Grade II Bio-safety Cabinet, whole blood was diluted in the ratio of 1:1 with DPBS (Dulbecco's Phosphate Buffered Saline). 100 μl of the diluted blood samples were taken and added to each of wells of a 96-well plate. 0.5 μl of compound solution was added to each well. The compound was formulated with dimethyl sulfoxide. The 96-well plate was placed in $CO_2$ incubator and incubated for 30 min, then lipopolysaccharide in final concentration of 100 ng/ml was added, and incubated overnight. The 96-well plate was shaked for homogenization, and from each well 10 μl of solution was taken and transferred to another 96-well plate for ELISA to measure TNF-α content. The following formula was used to calculate inhibition rate, and the inhibition rate was used for calculation of $IC_{50}$ value with XLfit.

Inhibition rate=[signal value (MAX)−signal value (sample)]×100/[signal value (MAX)−signal value (MIN)]

Notation: MAX represents blank control stimulated with only lipopolysaccharide; MIN represents positive control with 1 μmol/l of dexamethasone.

Experimental Results and Discussion:

TABLE 2

IC$_{50}$ values of compounds of the present invention for TNF-α in whole blood test

| Compound | TNF-α (nM) |
| --- | --- |
| Dexamethasone | 3.3 |
| MK-0873 | 40.3 |
| Compound 1 | 51.0 |
| Nitrogen oxide of Compound 1 | 109.1 |

Conclusion: Table 2 showed the compound of the present invention could effectively inhibit TNF-α release in whole blood.

EMBODIMENTS OF THE INVENTION

The above contents of the present invention are further illustrated by the following embodiments in form of examples, but the scope of the present invention is not limited to the following examples. All technologies fulfilled on basis of the contents of the present invention fall within the scope of the present invention.

Example 1

Preparation of N-cyclopropyl-4-oxo-1-[3-(pyridin-3-ylethynyl) phenyl]-1,4-dihydropyridino[2,3-c]pyridazine-3-formamide (Compound 1)

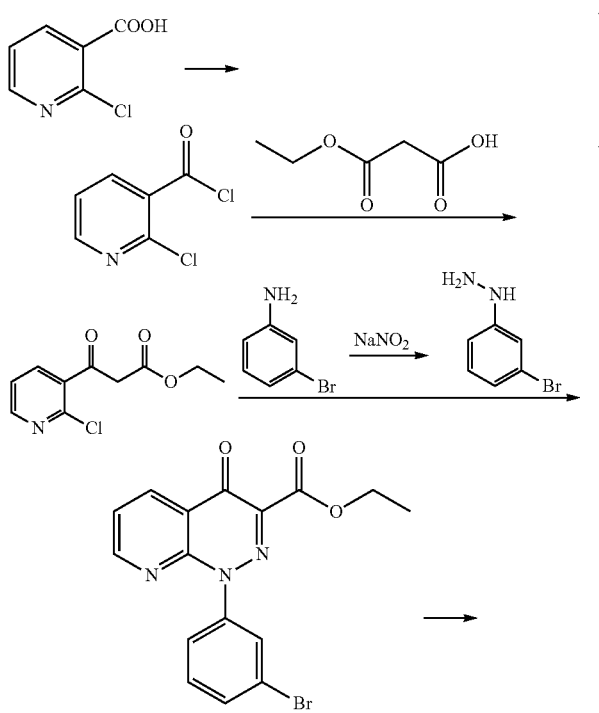

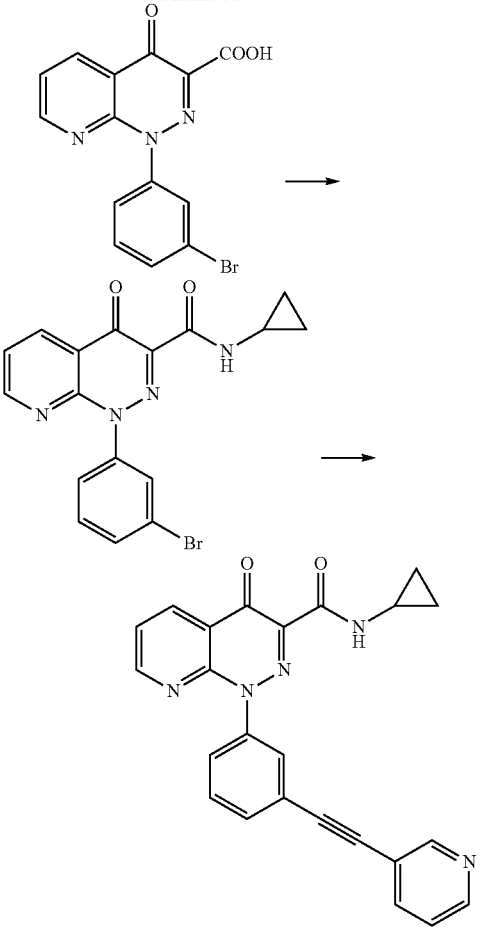

Step 1: Preparation of 2-chloronicotinoyl chloride

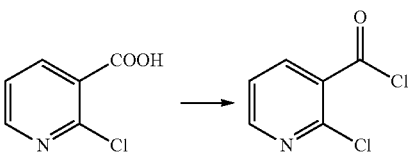

To 2-chloronicotinic acid (15.7 g, 100 mmol) in thionyl chloride (50 mL) was added DMF (0.2 mL), heated to 70° C. and reacted for 3 h. After reaction was complete, solvent was removed by distillation to obtain crude product 17.5 g.

Step 2: Preparation of 3-(2-chloropyridin-3-yl)-3-carbonylpropionic acid ethyl ester

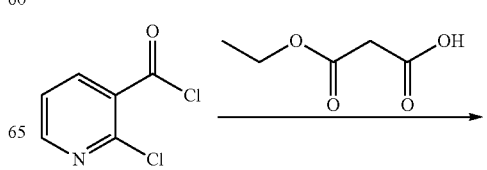

-continued

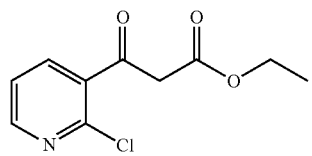

3-ethoxy-3-carbonylpropionic acid (13.2 g, 100 mmol) was dissolved in tetrahydrofuran (100 mL), n-butyl lithium (25.6 g, 400 mmol) was added dropwise at −78° C., reacted at low temperature for 1 h, 2-chloronicotinoyl chloride (17.5 g, 99.4 mmol) in tetrahydrofuran (20 mL) solution was added, and continuously reacted at low temperature for 3 h. After reaction was complete, extraction was performed with water/dichloromethane, organic phase was rotated for dryness, and separated by column chromatography to obtain product 13.8 g.

Step 3: Preparation of 1-(3-bromophenyl)-4-oxo-1,4-dihydropyridino[2,3-c]pyridazine-3-carboxylic acid ethyl ester

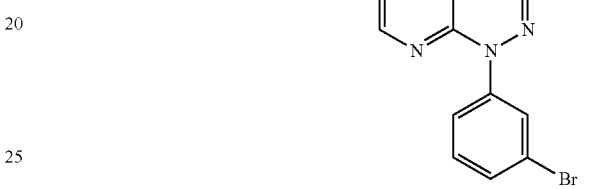

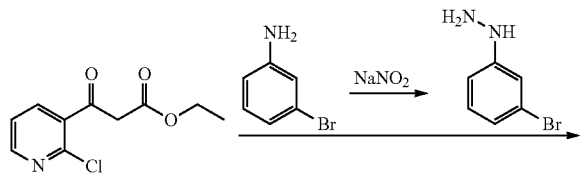

In ice-bath, to 3-bromophenylamine (3.87 g, 22.5 mmol) in 20% hydrochloric acid solution (15 mL) was added aqueous NaNO$_2$ (1.66 g, 24 mmol) solution, stirred for 30 min, then added to a mixture solution of 3-(2-chloropyridin-3-yl)-3-carbonylpropionic acid ethyl ester (3.4 g, 15 mmol), sodium acetate (9.85 g, 120.1 mmol) in ethanol (30 mL)/water (30 mL)/chloroform (30 mL), reacted in ice-bath for 15 min, heated to room temperature and reacted for 30 min. After reaction was complete, 30 mL water was added, separated, and organic phase was retained, rotated for dryness. Acetonitrile (50 mL) was added, K$_2$CO$_3$ (2.5 g, 18.1 mmol) was added, heated until refluxing, reacted for 3 h. After reaction was complete, solvent was removed by distillation, crystallization was performed with ethyl ether to obtain product 3.6 g.

Step 4: Preparation of 1-(3-bromophenyl)-4-oxo-1,4-dihydropyridino[2,3-c]pyridazine-3-carboxylic acid

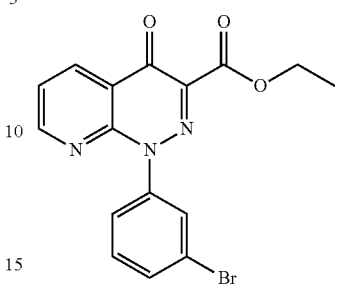

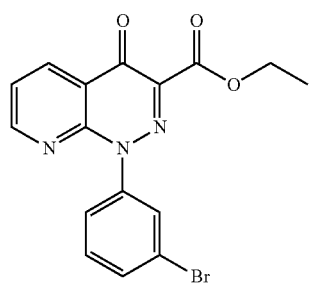

To 1-(3-Bromophenyl)-4-oxo-1,4-dihydropyridino[2,3-c]pyridazine-3-carboxylic acid ethyl ester (3.6 g, 9.6 mmol) in methanol(50 mL) was added potassium hydroxide (5.3 g, 94.6 mmol), heated to 65° C. and reacted for 3 h. Dilute hydrochloric acid was added to regulate pH to 5-6, solvent was removed by distillation, 50 mL water was added, filtrated to obtain product 3.25 g.

Step 5: Preparation of 1-(3-bromophenyl)-N-cyclopropyl-4-oxo-1,4-dihydropyridino[2,3-c]pyridazine-3-formamide

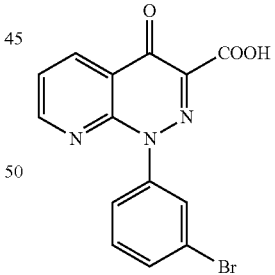

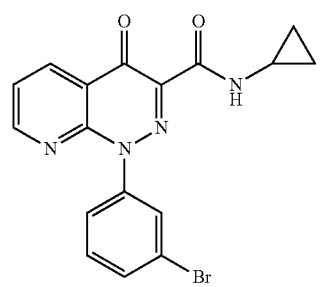

To 1-(3-bromophenyl)-4-oxo-1,4-dihydropyridino[2,3-c]pyridazine-3-carboxylic acid (3.25 g, 9.4 mmol) in dichloromethane (50 mL) was added triethylamine (2.37 g, 23.5 mmol), isopropyl chloroformate (1.49 g, 12.2 mmol), reacted at room temperature for 2 h, cyclopropylamine (0.54 g, 9.4 mmol) was added, reacted at room temperature overnight, extracted with H₂O/DCM, organic phase was rotated for dryness to obtain product 3.5 g.

Step 6: Preparation of N-cyclopropyl-4-oxo-1-[3-(pyridin-3-ylethynyl) phenyl]-1,4-dihydropyridino[2,3-c]pyridazine-3-formamide

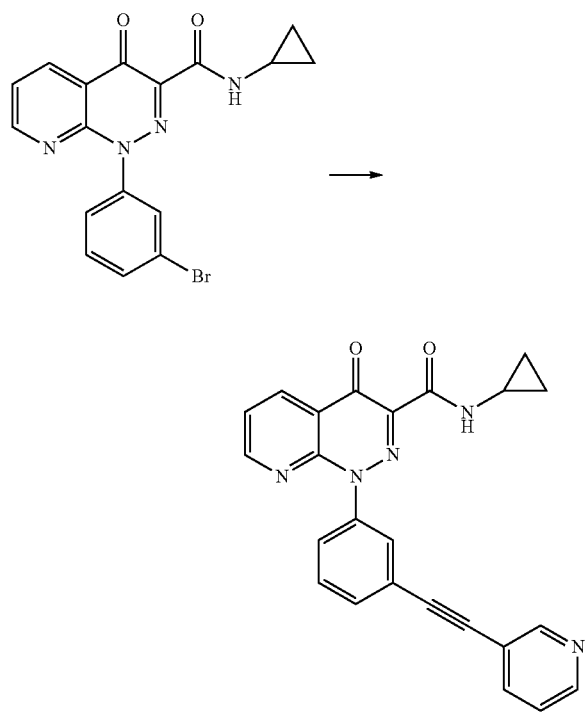

To 1-(3-Bromophenyl)-N-cyclopropyl-4-oxo-1,4-dihydropyridino[2,3-c]pyridazine-3-formamide (1 g, 2.6 mmol) in 50 mL DMSO was successively added 3-ethynyl-pyridine (0.34 g, 3.3 mmol), bistriphenylphosphine palladium dichloride (0.53 g, 0.76 mmol), CuI (0.14 g, 0.74 mmol), triethylamine (0.63 g, 6.25 mmol), reacted in a microwave reactor at 100° C. for 90 min. After reaction was complete, extraction was performed with H₂O/DCM, and organic phase was purified by preparation chromatography column to obtain product 0.2 g.

LC-MS: 408(M+H)⁺

¹H NMR (400 MHz, CDCl₃):δ 9.60 (s, 1H), 8.88 (d, J=4.4 Hz, 1H), 8.75-8.78 (m, 2H), 8.57 (d, J=4.8 Hz, 1H), 7.80-7.84 (m, 2H), 7.65-7.69 (m, 2H), 7.54~7.59 (m, 2H), 7.29~7.32 (m, 1H), 3.04~3.10 (m, 1H), 0.88~0.92 (m, 2H), 0.67~0.73 (m, 2H).

Example 2

Preparation of 3-[[3-[3-(cyclopropylcarbamoyl)-4-oxo-pyridino[2,3-c]pyridazine-1(4H)-yl]phenyl]ethynyl]pyridine-1-oxide (nitrogen oxide of Compound 1)

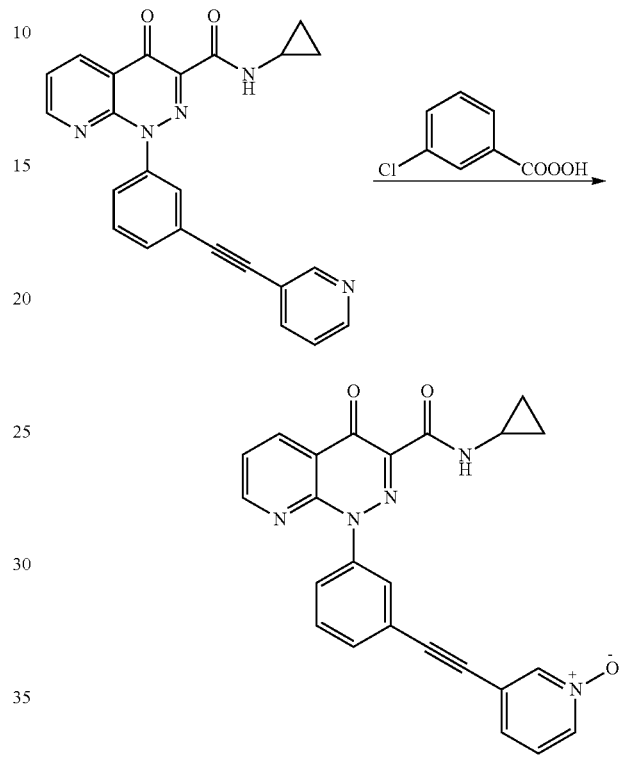

N-cyclopropyl-4-oxo-1-[3-(pyridin-3-ylethynyl)phenyl]-1,4-dihydropyridino[2,3-c]pyridazine-3-formamide (0.15 g, 0.36 mmol) was dissolved in 50 mL of dichloromethane solution, m-chloroperoxybenzoic acid (0.062 g, 0.36 mmol) was added and reacted at room temperature. After reaction was complete, separation was purified by liquid preparation chromatography column to obtain product 27 mg.

LC-MS: 424(M+H)⁺

¹H NMR (400 MHz, CDCl₃):δ 9.60 (s, 1H), 8.87 (d, J=4.4 Hz, 1H), 8.77 (d, J₁=6.4 Hz, J₂=8 Hz,1H), 8.34 (s, 1H), 8.19 (d, J=6.4 Hz, 1H), 7.85 (s, 1H), 7.67~7.71 (m, 2 H), 7.55~7.59 (m, 2H), 7.39~7.41 (m, 1H), 7.28~7.29 (m, 1H), 3.04~3.11 (m, 1H), 0.86~0.93 (m, 2H), 0.67~0.73 (m, 2H).

Example 3

Preparation of N-cyclopropyl-4-oxo-1-[3-(pyridin-3-ylthio) phenyl]-1,4-dihydropyridino[2,3-c]pyridazine-3-carboxamide (Compound 2)

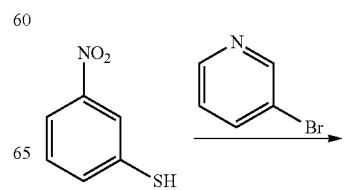

25

-continued

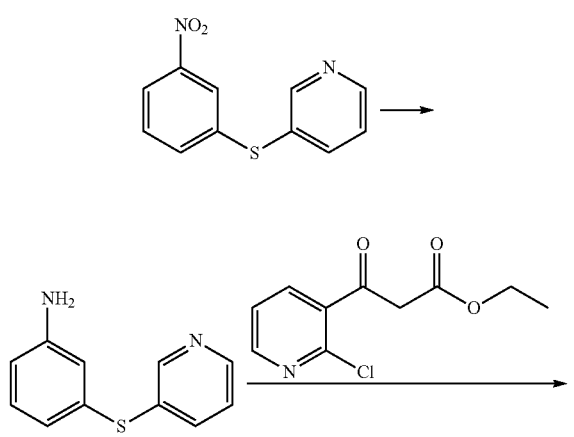

26

-continued

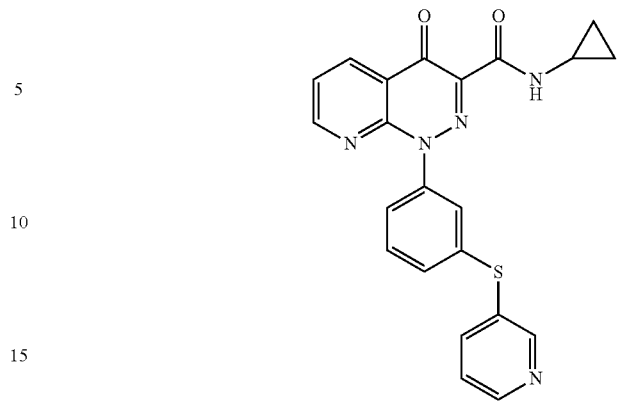

Step 1: Preparation of 3-(3-nitrophenylthio)pyridine

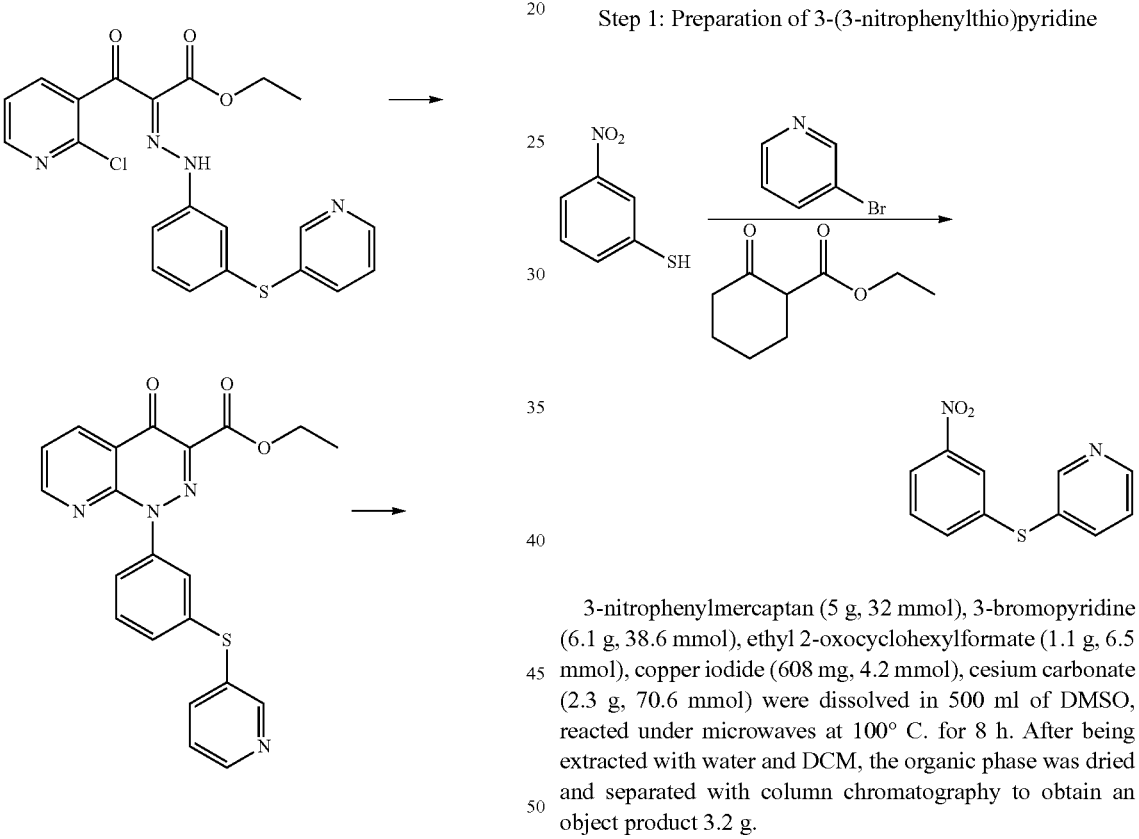

3-nitrophenylmercaptan (5 g, 32 mmol), 3-bromopyridine (6.1 g, 38.6 mmol), ethyl 2-oxocyclohexylformate (1.1 g, 6.5 mmol), copper iodide (608 mg, 4.2 mmol), cesium carbonate (2.3 g, 70.6 mmol) were dissolved in 500 ml of DMSO, reacted under microwaves at 100° C. for 8 h. After being extracted with water and DCM, the organic phase was dried and separated with column chromatography to obtain an object product 3.2 g.

Step 2: Preparation of 3-(pyridin-3-ylthio)aniline

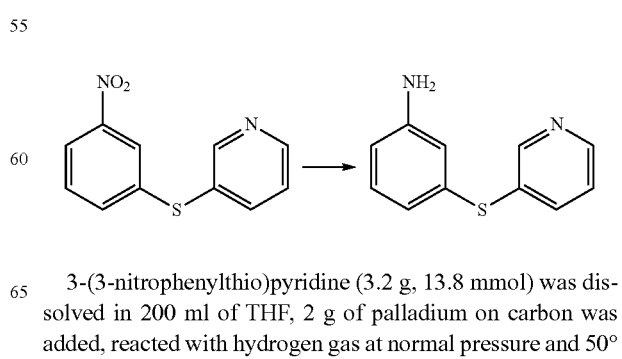

3-(3-nitrophenylthio)pyridine (3.2 g, 13.8 mmol) was dissolved in 200 ml of THF, 2 g of palladium on carbon was added, reacted with hydrogen gas at normal pressure and 50°

C. for 8 h. Suction filtration was carried out, and the reaction solution was concentrated to obtain an object product 2 g.

Step 3: Preparation of ethyl (Z)-3-(2-chloropyridin-3-yl)-3-oxo-2-(2-(3-(pyridin-3-ylthio)phenyl)hydrazino)propionate

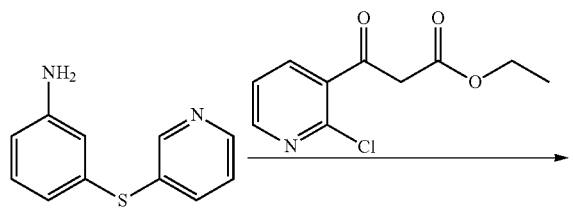

In ice-bath, to 3-(pyridin-3-ylthio)aniline (2 g, 10 mmol) in 20% hydrochloric acid solution was added an aqueous solution of sodium nitrite (1.1 g, 16 mmol), then immediately added to a mixture solution of ethyl 3-(2-chloropyridin-3-yl)-3-oxopropionate (3.4 g, 15 mmol), sodium acetate (6.5 g, 79 mmol), ethanol, water and chloroform, reacted in ice-bath for 1 h, then reacted at room temperature for 1 h. The reaction solution was extracted with DCM and water, and the organic phase was concentrated to obtain an object product 1.7 g.

Step 4: Preparation of ethyl 4-oxo-1-(3-(pyridin-3-ylthio) phenyl)-1,4-dihydropyridino[2,3-c]pyridazine-3-carboxylate

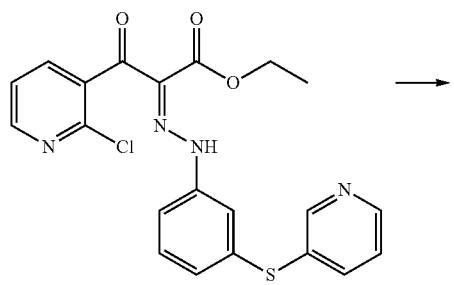

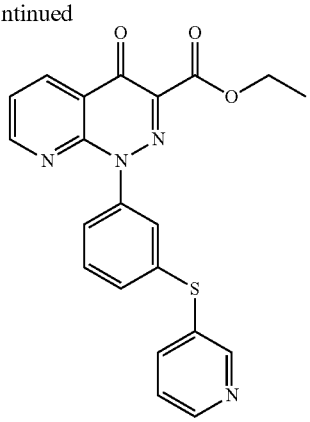

Ethyl (Z)-3-(2-chloropyridin-3-yl)-3-oxo-2-(2-(3-(pyridin-3-ylthio)phenyl) hydrazino)propionate (1.7 g, 3.86 mmol), and potassium carbonate (1.1 g, 7.96 mmol) were dissolved in 100 ml of acetonitrile, reacted under refluxing for 4 h, concentrated, crystalized with ethyl ether to obtain an object product 1.2 g.

Step 5: Preparation of 4-oxo-1-(3-(pyridin-3-ylthio) phenyl)-1,4-dihydropyridino[2,3-c]pyridazine-3-carboxylic acid

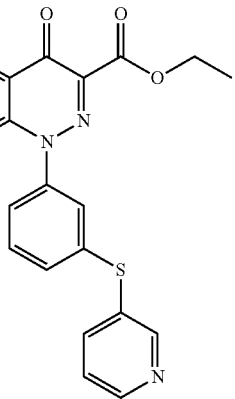

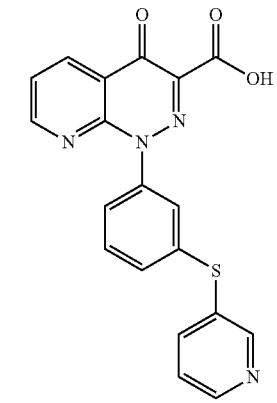

Ethyl 4-oxo-1-(3-(pyridin-3-ylthio)phenyl)-1,4-dihydropyridino[2,3-c]pyridazine-3-carboxylate (1.2 g, 3 mmol) was dispersed in 100 ml of methanol, KOH (840 mg, 15 mmol) was added, reacted at 40° C. for 4 h. The reaction solution was regulated with hydrochloric acid to pH 7, precipitated out solid, suction filtrated and dried to obtain an object product 200 mg.

Step 6: Preparation of N-cyclopropyl-4-oxo-1-[3-(pyridin-3-ylthio) phenyl]-1,4-dihydropyridino[2,3-c]pyridazine-3-formamide

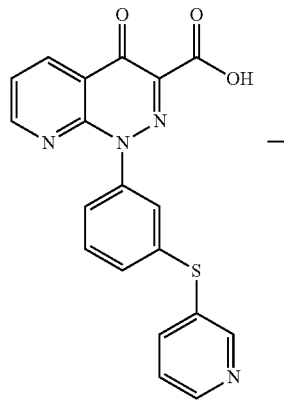

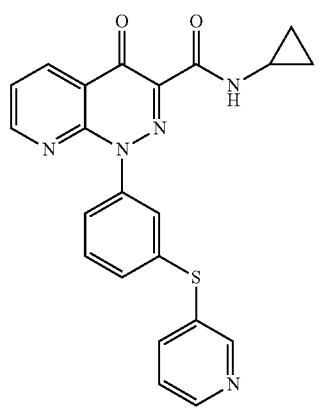

4-oxo-1-(3-(pyridin-3-ylthio)phenyl)-1,4-dihydropyridino[2,3-c]pyridazine-3-carboxylic acid (200 mg, 0.53 mmol) was dissolved in 100 ml of DCM, the following were added dropwise at −15° C. in order: TEA (133.8 mg, 1.325 mmol), isopropyl chlorocarbonate (97 mg, 0.792 mmol), and reacted at −15° C. for 0.5 h, then cyclopropylamine (36 mg, 0.631 mmol) was added dropwise, reacted at room temperature for 3 h. The reaction solution was washed with water, the organic phase was dried, concentrated and crystallized to obtain an object product 13.78 mg.

$^1$H NMR (400 MHz, CDCl$_3$): δ 9.55 (s, 1H), 8.83-8.84 (m, 1H), 8.73-8.75 (m, 2H), 8.51 (s, 1H), 7.60 (m, 1H), 7.57-7.59 (m, 1H), 7.56-7.57 (m, 1H), 7.53-7.54 (m, 1H), 7.49-7.51 (m, 1H), 7.43-7.49 (m, 1H), 7.30 (m, 1H), 3.03-3.08 (m, 1H), 0.87~0.92 (m, 2H), 0.67-0.71 (m, 2H).

Example 4

Preparation of 3-(3-(3-cyclopropylcarbamoyl)-4-oxo-pyridino[2,3-c]pyridazin-1(4H)-yl)phenyl)sulfuryl)pyridine 1-oxide (nitrogen oxide of Compound 4)

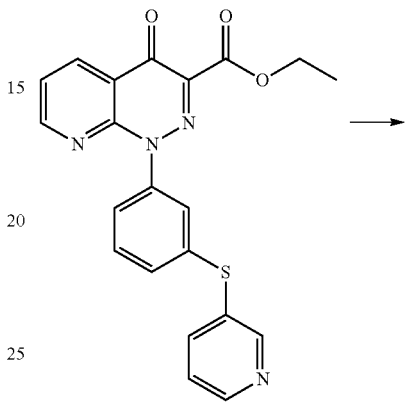

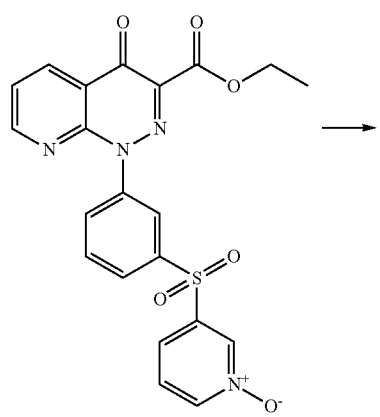

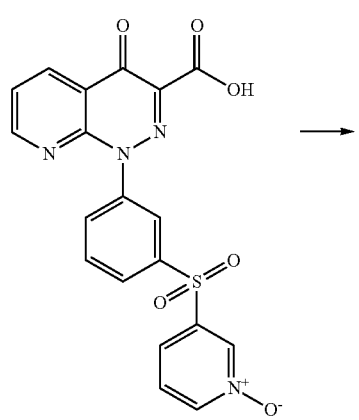

31
-continued

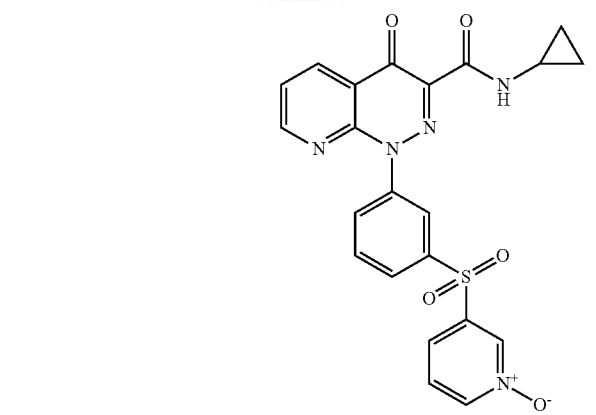

Step 1: Preparation of 3-(3-(3-ethoxycarbonyl)-4-oxo-pyridino[2,3-c]pyridazin-1(4H)-yl)phenylsulfuryl)pyridine 1-oxide

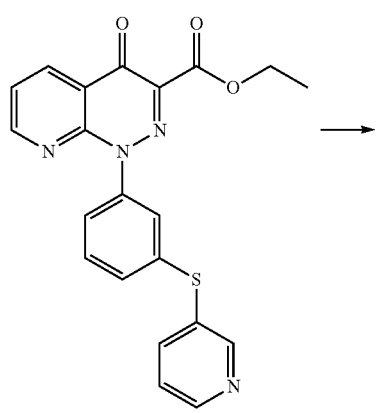

ethyl 4-oxo-1-(3-(pyridin-3-ylthio)phenyl)-1,4-dihydropyridino[2,3-c]pyridazine-3-formate (5.0 g, 12 mmol), m-chloroperbenzoic acid (10.3 g, 60 mmol) were dissolved in 500 ml of DCM, reacted at 30° C. for 5 h. Water was added for extraction, the organic phase was dried and concentrated to obtain an object product 4.6 g.

32

Step 2: Preparation of 3-(3-(3-carbonyl-4-oxo-pyridino[2,3-c]pyridazin-1 (4H)-yl)phenylsulfuryl)pyridine 1-oxide

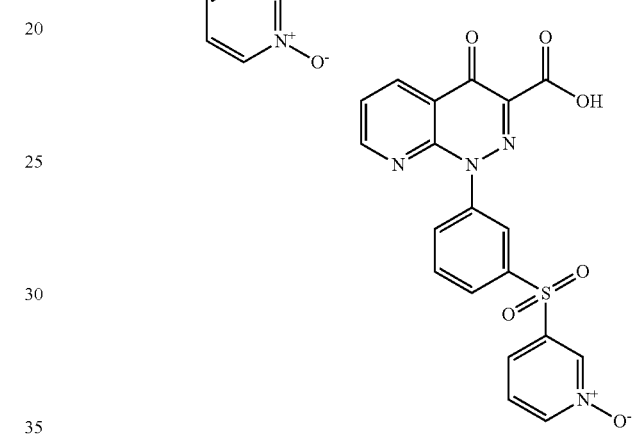

3-(3-(3-ethoxycarbonyl)-4-oxo-pyridino[2,3-c]pyridazin-1 (4H)-yl)phenyl sulfuryl)pyridine 1-oxide (4.6 g, 10 mmol) was dissolved in 100 ml of methanol, KOH (2.8 g, 50 mmol) was added, reacted at 40° C. for 4 h. The reaction solution was regulated with hydrochloric acid to pH 7, precipitated out solid, suction filtrated and dried to obtain an object product 1.3 g.

Step 3: Preparation of 3-(3-(3-cyclopropylcarbamoyl)-4-oxo-pyridino[2,3-c]pyridazin-1 (4H)-yl)phenylsulfuryl)pyridine 1-oxide

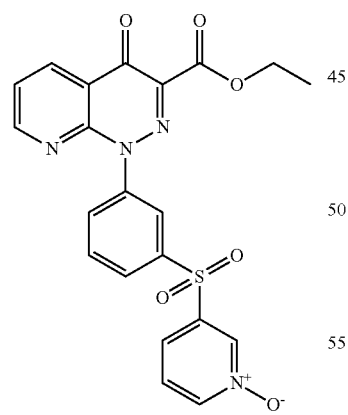

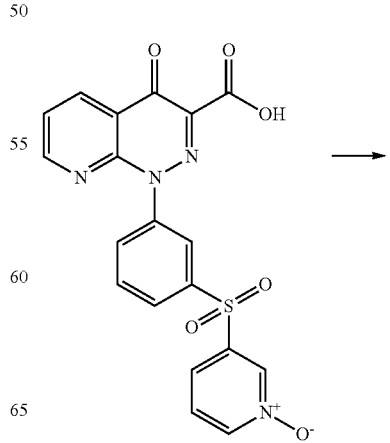

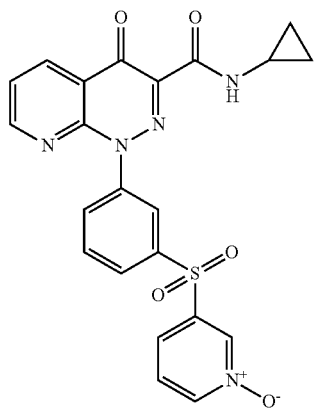

3-(3-(3-carbonyl-4-oxo-pyridino[2,3-c]pyridazin-1 (4H)-yl)phenylsulfuryl) pyridine 1-oxide (2.12 g, 5.0 mmol) was dissolved in 200 ml of DCM, the following were added dropwise at −15° C. in order: TEA (1.01 g, 10 mmol), isopropyl chloroformate (0.9 g, 7.3 mmol), and reacted at −15° C. for 1 h; then cyclopropylamine (342 mg, 6.0 mmol) was added dropwise, and reacted at room temperature for 3 h. The reaction solution was washed with water, the organic phase was dried, concentrated and separated by column chromatography to obtain an object product 400 mg.

LC-MS: 464(M+H)$^+$ $^1$H NMR (400 MHz, CDCl$_3$): δ 9.56 (s, 1H), 8.85-8.90 (m, 1H), 8.76-8.78 (m, 2H), 8.30-8.34 (s, 1H), 8.28-8.30 (m, 1H), 8.05-8.07 (m, 1H), 8.00-8.01 (m, 1H), 7.77-7.81 (m, 1H), 7.71-7.73 (m, 1H), 7.63-7.71 (m, 1H), 7.43-7.46 (m, 1H), 3.00-3.09 (m, 1H), 0.89-0.91 (m, 2H), 0.69-0.71 (m, 2H).

Example 5

Preparation of N-cyclopropyl-4-oxo-1-(3-(pyridin-3-yloxy) phenyl)-1,4-dihydropyridino[2,3-c]pyridazine-3-carboxamide (Compound 3)

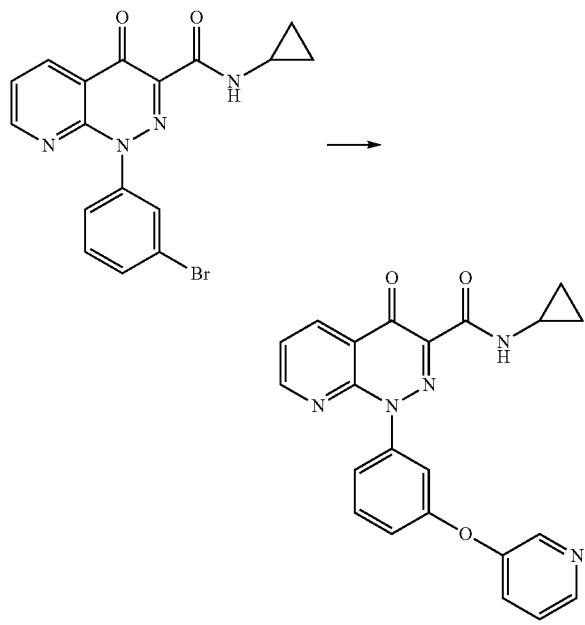

To N-cyclopropyl-4-oxo-1-[3-(pyridin-3-ylethynyl)phenyl]-1,4-dihydropyridino[2,3-c]pyridazine-3-formamide in 50 mL of DMSO was added in sequence 3-hydroxypyridine (0.48 g, 5 mmol), 2-oxocyclopentylcarboxylic acid ethyl ester (0.3 g, 2 mmol), CuI (0.4 g, 2 mmol), Cs$_2$CO$_3$ (2.6 g, 8 mmol), reacted in microwave reactor at 120° C. for 6 h. After reaction was complete, extraction was performed with H$_2$O/DCM, and organic phase was separated to obtain product 26 mg.

LC-MS: 400(M+H)$^+$ $^1$H NMR (400 MHz, CDCl$_3$):δ 9.60 (s, 1H), 8.86 (d, J=4.4 Hz, 1H), 8.75 (dd, J$_1$=6.4 Hz, J$_2$=8 Hz,1H), 8.52 (s, 1H), 8.41 (d, J=4.4 Hz, 1H), 7.53~7.57 (m, 2H), 7.42~7.44 (m, 2H), 7.30~7.33 (m, 2H), 7.15~7.18 (m, 1H), 3.03~3.09 (m, 1H), 0.86~0.93 (m, 2H), 0.67~0.73 (m, 2H).

Example 6

Preparation of 3-(3-(3-cyclopropylcarbamoyl)-4-oxo-pyridino[2,3-c]pyridazin-1(4H)-yl)phenoxyl) pyridine 1-oxide (nitrogen oxide of Compound 3)

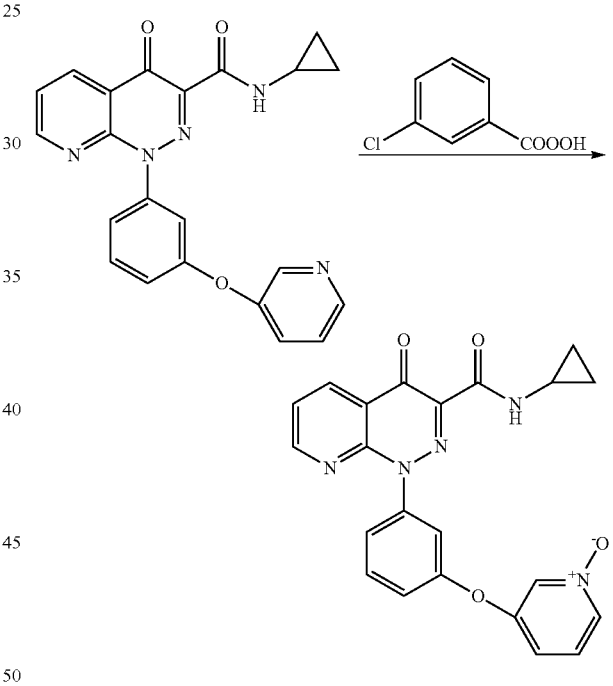

To N-cyclopropyl-4-oxo-1-(3-(pyridin-3-yloxy)phenyl)-1,4-dihydropyridino[2,3-c]pyridazine-3-formamide (0.72 g, 1.8 mmol) in DCM (30 ml), 3-chloroperbenzoic acid (0.31 g, 1.8 mmol) was added, reacted at 30° C. for 5 h. After the end of reaction, the reaction was washed with H$_2$O (10 ml×2), the organic phase was dried by rotation to obtain a solid, which was washed with ethyl ether (5 ml×2) to obtain an object product 0.415 g.

LC-MS: 416(M+H)$^+$ $^1$H NMR (400 MHz, CDCl$_3$): δ 9.58-9.59 (d, J=4 Hz, 1H), 8.90-8.91 (m, 1H), 8.74-8.76 (m, 1H), 8.17-8.18 (t, J=4 Hz, 1H), 8.00-8.01 (d, J=4 Hz, 1H), 7.54-7.62 (m, 3H), 7.41-7.42 (t, J=4 Hz, 1H), 7.21-7.24 (m, 2H), 7.02-7.04 (m, 1H), 3.03 -3.08 (m, 1H), 0.87-0.92 (m, 2H), 0.67-0.71 (m, 2H).

According to the above preparation methods, the following compounds were prepared as well:

| Compound | Structural formula | Mass spectrum (M + H)+ |
|---|---|---|
| 5 | | 432 |
| Nitrogen oxide of 5 | | 448 |
| 6 | | 410 |
| Nitrogen oxide of 6 | | 426 |
| 7 | | 410 |
| Nitrogen oxide of 7 | | 426 |
| 8 | | 514 |
| Nitrogen oxide of 8 | | 530 |

-continued

| Compound | Structural formula | Mass spectrum (M + H)+ |
|---|---|---|
| 9 | (structure) | 506 |
| Nitrogen oxide of 9 | (structure) | 522 |
| 10 | (structure) | 522 |
| Nitrogen oxide of 10 | (structure) | 538 |
| 11 | (structure) | 538 |
| Nitrogen oxide of 11 | (structure) | 554 |
| 12 | (structure) | 554 |
| Nitrogen oxide of 12 | (structure) | 570 |

-continued

| Compound | Structural formula | Mass spectrum $(M + H)^+$ |
|---|---|---|
| 13 | 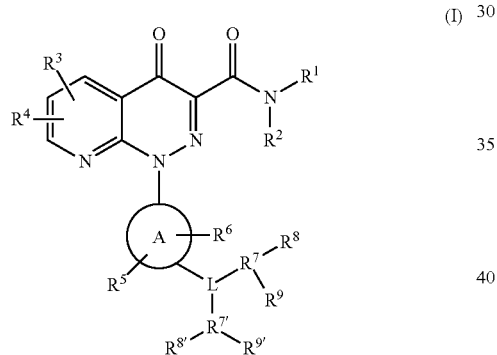 | 569 |

What is claimed is:

1. A compound of Formula (I), or a pharmaceutically acceptable salt or a stereoisomer thereof, wherein Formula (I) is:

(I)

wherein $R^1$ is hydrogen, $C_{1-8}$ alkyl optionally substituted with 1-3 substituents, $C_{1-8}$ alkoxy optionally substituted with 1-3 substituents, $C_{3-8}$ cycloalkyl optionally substituted with 1-3 substituents, $C_{2-8}$ alkenyl optionally substituted with 1-3 substituents, $C_{3-8}$ alkynyl optionally substituted with 1-3 substituents, —C(O)—$R^a$, —S(O)$_q$—$R^a$, $C_{6-14}$ aryl each optionally substituted with 1-3 substituents, 5-15-membered heteroaryl optionally substituted with 1-3 substituents, or 3-15-membered heterocyclyl-$C_{1-8}$ alkyl optionally substituted with 1-3 substituents;

$R^2$ is hydrogen, $C_{1-8}$ alkyl optionally substituted with 1-3 substituents, or $C_{3-8}$ cycloalkyl optionally substituted with 1-3 substituents;

each of $R^3$, $R^4$, $R^5$ and $R^6$ independently is hydrogen, halogen, $C_{1-8}$ alkyl optionally substituted with 1-3 substituents, $C_{1-8}$ alkoxy optionally substituted with 1-3 substituents, —C(O)—$R^a$, —S(O)$_q$—$R^a$, nitro, cyano, or —NR$^a$R$^{a\prime}$;

$R^7$ is phenyl, thienyl, pyridonyl, oxazolyl, oxadiazolyl, thiazolyl, or thiadiazolyl, each optionally substituted with 1-3 substituents; pyridyl, pyrimidyl, indolyl, quinolyl, or imidazolyl or a nitrogen oxide thereof, each optionally substituted with 1-3 substituents; hydrogen; $C_{1-8}$ alkyl optionally substituted with 1-3 substituents; or $C_{3-8}$ cycloalkyl optionally substituted with 1-3 substituents;

$R^{7\prime}$ is absent, or is phenyl, thienyl, pyridonyl, oxazolyl, oxadiazolyl, thiazolyl, or thiadiazolyl, each optionally substituted with 1-3 substituents; pyridyl, pyrimidyl, indolyl, quinolyl, or imidazolyl or a nitrogen oxide thereof, each optionally substituted with 1-3 substituents; hydrogen; $C_{1-8}$ alkyl optionally substituted with 1-3 substituents; or $C_{3-8}$ cycloalkyl optionally substituted with 1-3 substituents;

$R^8$ is hydrogen, halogen, nitro, cyano, =N—O—$C_{1-8}$ alkyl, —O—N=$C_{1-8}$ alkyl, —CH(N=NOH)—$C_{1-8}$ alkyl, $C_{1-8}$ alkyl each optionally substituted with 1-3 substituents, $C_{3-8}$ cycloalkyl optionally substituted with 1-3 substituents, $C_{1-8}$ alkoxy optionally substituted with 1-3 substituents, $C_{6-14}$ aryl optionally substituted with 1-3 substituents, 5-15-membered heteroaryl optionally substituted with 1-3 substituents, 3-15-membered heterocyclyl$C_{1-8}$ alkyl optionally substituted with 1-3 substituents, —NR$^a$R$^{a\prime}$, —C(O)—$R^a$, —C(O)NR$^a$R$^{a\prime}$, —NR$^a$C(O)R$^{a\prime}$, —S(O)$_q$—$R^a$, —S(O)$_q$—NR$^a$R$^{a\prime}$, —NR$^a$—S(O)$_q$—$R^{a\prime}$, or —C(O)OR$^a$;

$R^{8\prime}$ is absent, or is hydrogen, halogen, nitro, cyano, =N—O—$C_{1-8}$ alkyl, —O—N=$C_{1-8}$ alkyl, —CH(N=NOH)—$C_{1-8}$ alkyl, $C_{1-8}$ alkyl optionally substituted with 1-3 substituents, $C_{3-8}$ cycloalkyl optionally substituted with 1-3 substituents, $C_{1-8}$ alkoxy optionally substituted with 1-3 substituents, $C_{6-14}$ aryl optionally substituted with 1-3 substituents, 5-15-membered heteroaryl optionally substituted with 1-3 substituents, 3-15-membered heterocyclyl$C_{1-8}$ alkyl optionally substituted with 1-3 substituents, —NR$^a$R$^{a\prime}$, —C(O)—$R^a$, —C(O)NR$^a$R$^{a\prime}$, —NR$^a$C(O)R$^{a\prime}$, —S(O)$_q$—$R^a$, —S(O)$_q$—NR$^a$R$^{a\prime}$, —NR$^a$—S(O)$_q$—$R^{a\prime}$, or —C(O)OR$^a$;

$R^9$ is hydrogen, hydroxy, halogen, $C_{1-8}$ alkyl optionally substituted with 1-3 substituents, or —NR$^b$R$^{b\prime}$;

$R^{9\prime}$ is absent, or is hydrogen, hydroxy, halogen, $C_{1-8}$ alkyl optionally substituted with 1-3 substituents, or —NR$^b$R$^{b\prime}$;

ring A is phenyl, 5-8-membered heteroaryl containing 1-4 heteroatoms selected from N, S and O, or 8-14-membered bicyclic heterocyclyl group containing 1-4 heteroatoms selected from N, S and O;

L is

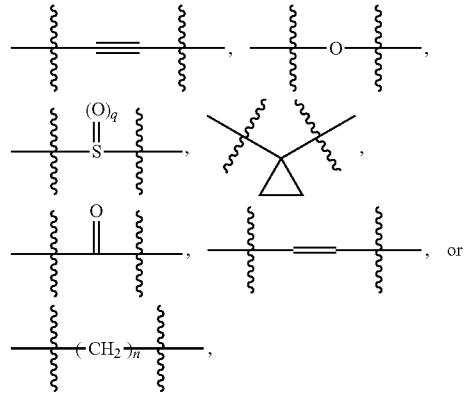

q is 0, 1 or 2;

n is 1, 2, 3 or 4; and $R^a$ and $R^{a'}$ are independently selected from hydrogen, $C_{1-8}$ alkyl optionally substituted with 1-3 substituents, $C_{3-8}$ cycloalkyl optionally substituted with 1-3 substituents, $C_{3-8}$ cycloalkyl $C_{1-8}$ alkyl optionally substituted with 1-3 substituents, $C_{6-14}$ aryl optionally substituted with 1-3 substituents, or 3-15-membered heterocyclyl group, optionally substituted with 1-3 substituents;

wherein the substituent of the substituted $C_{1-8}$ alkyl, substituted $C_{1-8}$ alkoxy, substituted $C_{2-8}$ alkenyl, substituted $C_{3-8}$ alkynyl, substituted $C_{3-8}$ cycloalkyl, substituted $C_{3-8}$ cycloalkyl $C_{1-8}$ alkyl, substituted $C_{6-14}$ aryl, substituted 5-15-membered heteroaryl, substituted 3-15-membered heterocyclyl group, substituted 3-15-membered heterocyclyl $C_{1-8}$ alkyl, substituted phenyl, pyridyl, pyrimidyl, indolyl, quinolyl, thienyl, pyridonyl, oxazolyl, oxadiazolyl, thiazolyl, thiadiazolyl, or imidazolyl refers to one or more groups independently selected from hydroxy, carboxy, nitro, cyano, halogen, $C_{1-8}$ alkyl, $C_{3-8}$ cycloalkyl, $C_{1-8}$ alkoxy, halogenated $C_{1-8}$ alkyl, halogenated $C_{1-8}$ alkoxy, —$NR^bR^{b'}$, —$C(O)$—$R^b$, —$C(O)NR^bR^{b'}$, —$NR^bC(O)R^{b'}$, =N—O—$C_{1-8}$ alkyl, —O—N=$C_{1-8}$ alkyl, —$S(O)_q$—$R^b$, —$S(O)_q$—$NR^bR^{b'}$, —$NR^b$—$S(O)_q$—$R^{b'}$, or —$C(O)OR^b$, wherein each of $R^b$ and $R^{b'}$ independently is hydrogen, $C_{1-8}$ alkyl, $C_{3-8}$ cycloalkyl or $C_{6-14}$ aryl.

2. The compound according to claim 1, or a pharmaceutically acceptable salt or a stereoisomer thereof:
wherein ring A is phenyl, or 5-6-membered heteroaryl containing 1-3 heteroatoms selected from N, S and O.

3. The compound according to claim 2, or a pharmaceutically acceptable salt or a stereoisomer thereof:
wherein
ring A is phenyl, or 5-6-membered heteroaryl containing 1-3 N heteroatoms.

4. The compound according to claim 3, or a pharmaceutically acceptable salt or a stereoisomer thereof:
wherein
ring A is phenyl, pyrrolyl, imidazolyl, pyrazolyl, triazolyl, pyridyl, pyrimidyl or pyrazinyl.

5. The compound according to claim 1, or a pharmaceutically acceptable salt or a stereoisomer thereof:
wherein $R^1$ is hydrogen, $C_{1-8}$ alkyl optionally substituted with 1-3 substituents, $C_{1-8}$ alkoxy optionally substituted with 1-3 substituents, $C_{3-8}$ cycloalkyl optionally substituted with 1-3 substituents, —$C(O)$—$R^a$, —$S(O)_q$—$R^a$, $C_{6-14}$ aryl optionally substituted with 1-3 substituents, or 5-15-membered heteroaryl optionally substituted with 1-3 substituents;

$R^2$ is hydrogen, or $C_{1-8}$ alkyl optionally substituted with 1-3 substituents;

each of $R^3$, $R^4$, $R^5$ and $R^6$ independently is hydrogen, halogen, $C_{1-8}$ alkyl optionally substituted with 1-3 substituents, $C_{1-8}$ alkoxy optionally substituted with 1-3 substituents, —$C(O)$—$R^a$, —$S(O)_q$—$R^a$, nitro, cyano, or —$NR^aR^{a'}$;

$R^7$ is phenyl, thienyl, pyridonyl, oxazolyl, oxadiazolyl, thiazolyl, or thiadiazolyl, each optionally substituted with 1-3 substituents; pyridyl, pyrimidyl, indolyl, quinolyl, or imidazolyl or a nitrogen oxide thereof, each optionally substituted with 1-3 substituents;

$R^{7'}$ is absent, or is phenyl, thienyl, pyridonyl, oxazolyl, oxadiazolyl, thiazolyl, or thiadiazolyl, each optionally substituted with 1-3 substituents; pyridyl, pyrimidyl, indolyl, quinolyl, or imidazolyl or a nitrogen oxide thereof, each optionally substituted with 1-3 substituents;

$R^8$ is hydrogen, halogen, $C_{1-8}$ alkyl optionally substituted with 1-3 substituents, —$NR^aR^{a'}$, —$C(O)$—$R^a$, —$C(O)NR^aR^{a'}$, —$NR^aC(O)R^{a'}$, —$S(O)_q$—$R^a$, —$S(O)_q$—$NR^aR^{a'}$, —$NR^a$—$S(O)_q$—$R^{a'}$, or —$C(O)OR^a$;

$R^{8'}$ is absent, or is hydrogen, halogen, $C_{1-8}$ alkyl optionally substituted with 1-3 substituents, —$NR^aR^{a'}$, —$C(O)$—$R^a$, —$C(O)NR^aR^{a'}$, —$NR^aC(O)R^{a'}$, —$S(O)_q$—$R^a$, —$S(O)_q$—$NR^aR^{a'}$, —$NR^a$—$S(O)_q$—$R^{a'}$, or —$C(O)OR^a$;

$R^9$ is hydrogen, hydroxy, halogen, $C_{1-8}$ alkyl optionally substituted with 1-3 substituents;

$R^{9'}$ is absent, or is hydrogen, hydroxy, halogen, $C_{1-8}$ alkyl optionally substituted with 1-3 substituents;

ring A is phenyl, 5-8-membered heteroaryl containing 1-4 heteroatoms selected from N, S and O, or 8-14-membered bicyclic heterocyclyl group containing 1-4 heteroatoms selected from N, S and O;

L is

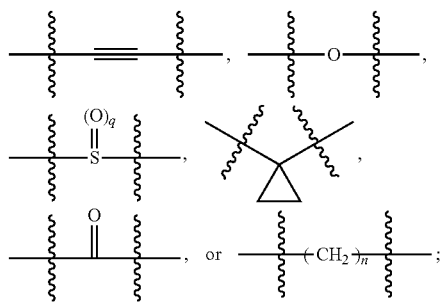

q is 0, 1 or 2;

n is 1 or 2; and $R^a$ and $R^{a'}$ are independently selected from hydrogen, $C_{1-8}$ alkyl optionally substituted with 1-3 substituents;

wherein the substituent of the substituted $C_{1-8}$ alkyl, substituted $C_{1-8}$ alkoxy, substituted $C_{3-8}$ cycloalkyl, substituted $C_{6-14}$ aryl, substituted 5-15-membered heteroaryl, substituted 3-15-membered heterocyclyl $C_{3-8}$ alkyl, substituted phenyl, pyridyl, pyrimidyl, indolyl, quinolyl, thienyl, pyridonyl, oxazolyl, oxadiazolyl, thiazolyl, thiadiazolyl, or imidazolyl refers to one or more groups independently selected from hydroxy, carboxy, cyano, halogen, $C_{1-8}$ alkyl, $C_{3-8}$ cycloalkyl, $C_{1-8}$ alkoxy, halogenated $C_{1-8}$ alkoxy, —$NR^bR^{b'}$, —$C(O)$—$R^b$, —$C(O)NR^bR^{b'}$, —$NR^bC(O)R^{b'}$, —$S(O)_q$—$R^b$, —$S(O)_q$—$NR^bR^{b'}$, —$NR^b$—$S(O)_q$—$R^{b'}$, or —$C(O)OR^b$, wherein each of $R^b$ and $R^{b'}$ independently is hydrogen or $C_{1-8}$ alkyl.

6. The compound according to claim 5, or a pharmaceutically acceptable salt or a stereoisomer thereof:

wherein $R^1$ is hydrogen, methyl, ethyl, propyl, isopropyl, cyclopropyl, cyclobutyl, or cyclopentyl;

$R^2$ is hydrogen, or methyl;

each of $R^3$, $R^4$, $R^5$ and $R^6$ independently is hydrogen, methyl, fluoro, chloro, or bromo;

each of $R^8$ and $R^9$ independently is hydrogen, methyl, fluoro, chloro, methylsulfonyl, or 2-hydroxyisopropyl;

$R^{7'}$ is absent;

$R^{8'}$ is absent; and $R^{9'}$ is absent.

7. The compound according to claim 1, or a pharmaceutically acceptable salt or a stereoisomer thereof:

wherein L is

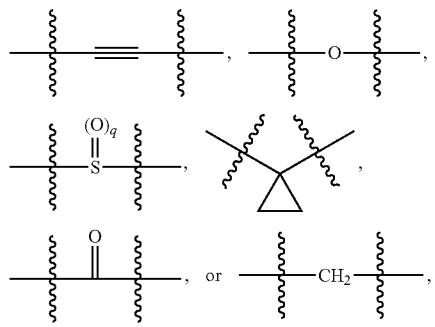

and q is 0, 1 or 2.

8. The compound according to claim 7, or a pharmaceutically acceptable salt or a stereoisomer thereof:

wherein
L is

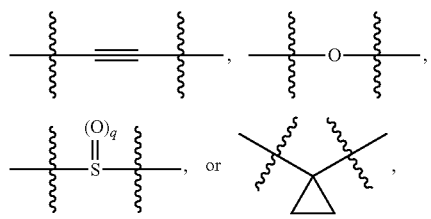

and q is 0, 1 or 2.

9. The compound according to claim 1, or a pharmaceutically acceptable salt or a stereoisomer thereof:

wherein $R^7$ is pyridyl or a nitrogen oxide thereof.

10. The compound according to claim 1, or a pharmaceutically acceptable salt or a stereoisomer thereof:

wherein $R^7$ is pyridyl or a nitrogen oxide thereof, ring A is phenyl, pyridyl, pyrimidyl or pyrazinyl;

L is

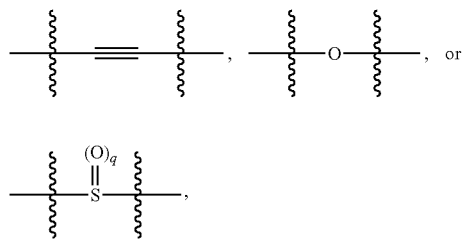

and q is 0, 1 or 2.

11. The compound according to claim 10, or a pharmaceutically acceptable salt or a stereoisomer thereof, wherein the compound is selected from:

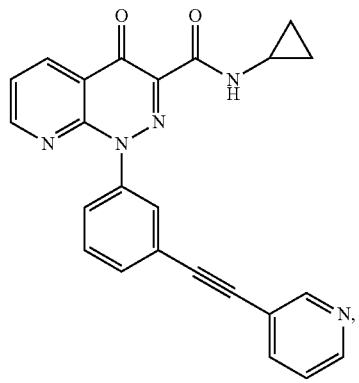

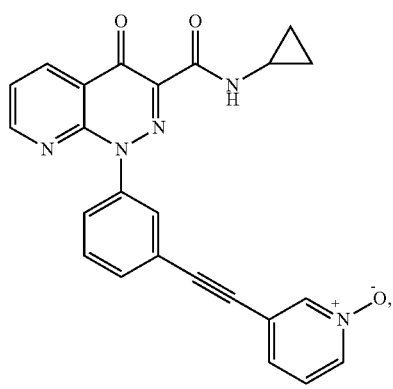

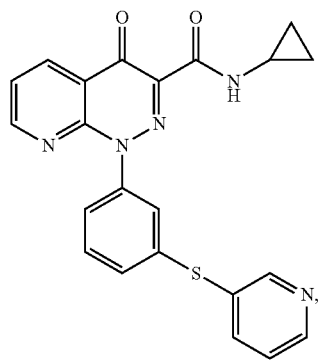

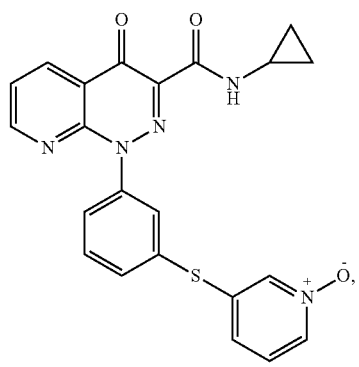 [SMILES: O=C(NC1CC1)c1nn(-c2cccc(Sc3ccc[n+]([O-])c3)c2)c2ncccc2c1=O]

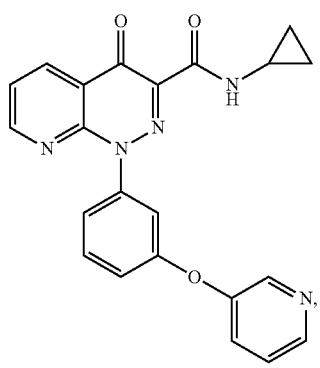
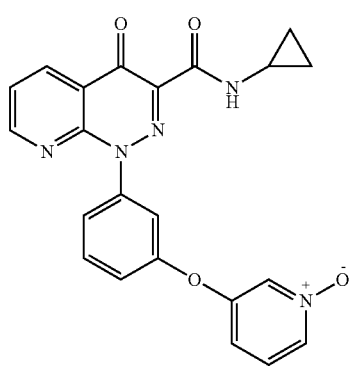
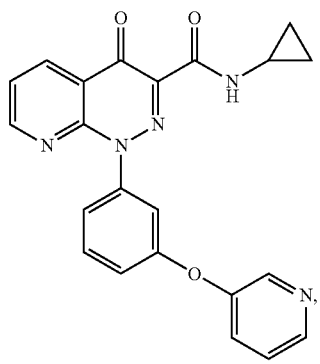
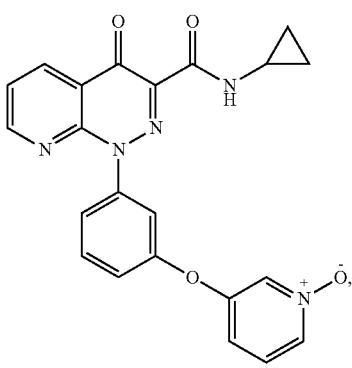 [SMILES: O=C(NC1CC1)c1nn(-c2cccc(Oc3ccc[n+]([O-])c3)c2)c2ncccc2c1=O]
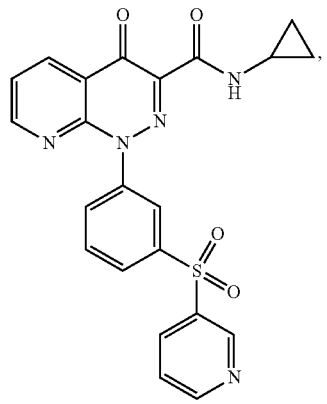
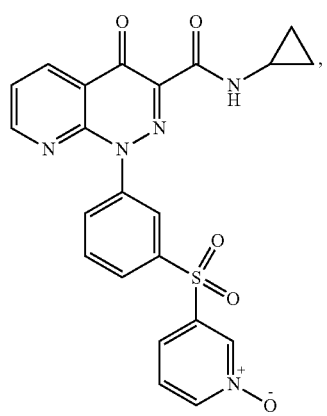
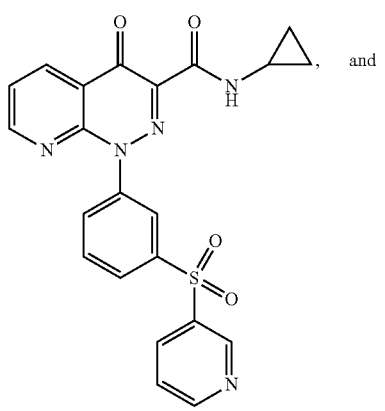
and
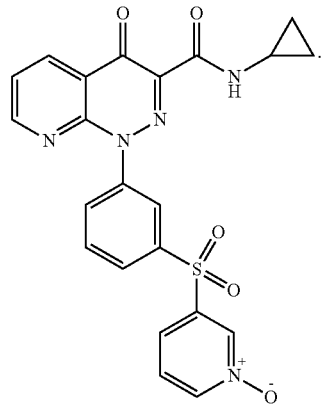

12. A pharmaceutical composition comprising a compound according to claim 1, or a pharmaceutically acceptable salt or a stereoisomer thereof and one or more pharmaceutically acceptable carriers and/or diluents.

13. A method for inhibiting tumor necrosis factor alpha activity and/or phosphodiesterase 4 activity in a subject, comprising administering to the subject a therapeutically effective amount of a compound of Formula (I) according to claim 1, or a pharmaceutically acceptable salt or a stereoisomer thereof.

14. The method according to claim 13, wherein the subject suffers from an inflammatory condition or immune condition chosen from asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohn's disease, psoriasis, urticarial, adult vernal conjunctivitis, respiratory distress, rheumatoid arthritis of spine, osteoarthritis, gouty arthritis, uveitis, allergic conjunctivitis, inflammatory bowel diseases, ulcerative colitis, eczema, atopic dermatitis, chronic inflammations, allergic inflammatory diseases, and inflammatory diseases or immune symptoms of the lung, joints, eyes, intestines, skin and heart.

15. A method of manufacturing a compound of Formula (I) according to claim 1, wherein said method comprises the steps of:
(i) reacting the following compound:

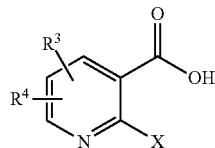

wherein X is chloro,
with thionyl chloride to form a compound of formula A:

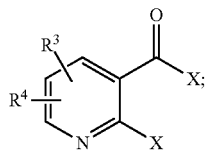

wherein each X is chloro;
(ii) reacting the compound of Formula A with 3-ethoxy-3-oxopropanoic acid to form a compound of formula B:

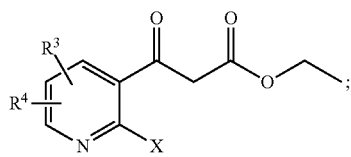

wherein X is chloro;

(iii) reacting the compound of Formula B with the following compound:

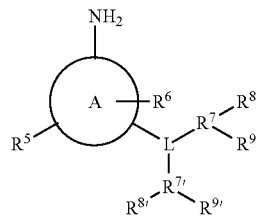

in the presence of sodium nitrite and hydrochloric acid to form a compound of Formula C:

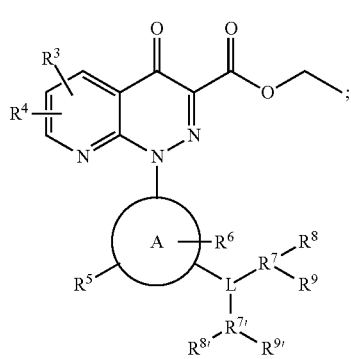

(iv) reacting the compound of Formula C with potassium hydroxide followed by hydrochloric acid to form a compound of Formula D:

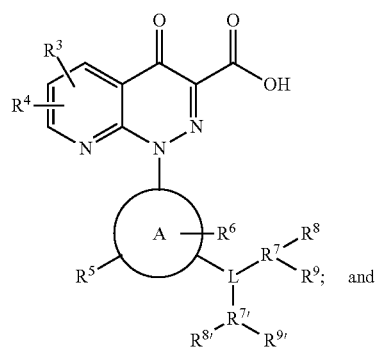

(v) reacting the compound of Formula D with triethylamine, isopropyl chloroformate, and $HNR^1R^2$ to form the compound of Formula (I) according to claim 1.

* * * * *